US011497630B2

(12) United States Patent
Huang et al.

(10) Patent No.: US 11,497,630 B2
(45) Date of Patent: Nov. 15, 2022

(54) INTELLIGENT PROSTHETIC SOCKET

(71) Applicant: Case Western Reserve University, Cleveland, OH (US)

(72) Inventors: Ming-Chun Huang, Pepper Pike, OH (US); Hongping Zhao, Beachwood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 118 days.

(21) Appl. No.: 16/378,762

(22) Filed: Apr. 9, 2019

(65) Prior Publication Data

US 2019/0307584 A1    Oct. 10, 2019

Related U.S. Application Data

(60) Provisional application No. 62/654,775, filed on Apr. 9, 2018.

(51) Int. Cl.
| | |
|---|---|
| *A61F 2/80* | (2006.01) |
| *A61F 2/60* | (2006.01) |
| *A61B 5/00* | (2006.01) |
| *A61F 2/76* | (2006.01) |
| *A61F 2/68* | (2006.01) |
| *A61F 2/70* | (2006.01) |

(52) U.S. Cl.
CPC .............. *A61F 2/80* (2013.01); *A61B 5/4851* (2013.01); *A61F 2/60* (2013.01); *A61F 2002/607* (2013.01); *A61F 2002/6827* (2013.01); *A61F 2002/705* (2013.01); *A61F 2002/769* (2013.01); *A61F 2002/7635* (2013.01); *A61F 2002/7665* (2013.01); *A61F 2310/00185* (2013.01)

(58) Field of Classification Search
CPC ........................................................ A61F 2/80
See application file for complete search history.

(56) References Cited

U.S. PATENT DOCUMENTS

| | | | | |
|---|---|---|---|---|
| 6,500,210 B1 * | 12/2002 | Sabolich | ................. | A61F 2/583 623/24 |
| 2004/0105810 A1 * | 6/2004 | Ren | ........................ | B82Y 30/00 423/624 |

(Continued)

OTHER PUBLICATIONS

Baek, Seong-Ho, and Il-Kyu Park. "Flexible piezoelectric nanogenerators based on a transferred ZnO nanorod/Si micro-pillar array." Nanotechnology 28.9 (2017): 095401.

(Continued)

*Primary Examiner* — Jacqueline Woznicki
(74) *Attorney, Agent, or Firm* — Tarolli, Sundheim, Covell & Tummino LLP

(57) ABSTRACT

A system can be used to record real-time pressure and/or shear force data within a socket for a prosthetic device. The system includes a socket for a prosthetic device that can be designed to fit a patient's residual limb. The system also includes a sensor array that can be placed within the socket for the prosthetic device to detect pressure and/or shear force on the patient's residual limb. The sensor array includes a piezo-electric material and a uniform distribution of a plurality of metal pads on either side of the piezo-electric material. Each of the plurality of metal pads on either side of the piezo-electric material comprises at least one wire connected to a common port.

10 Claims, 19 Drawing Sheets

(56) References Cited

U.S. PATENT DOCUMENTS

| | | | | |
|---|---|---|---|---|
| 2007/0055383 | A1* | 3/2007 | King | A61F 2/80 623/34 |
| 2007/0191965 | A1* | 8/2007 | Colvin | A61F 2/80 623/34 |
| 2007/0255424 | A1* | 11/2007 | Leydet | A61F 2/76 623/24 |
| 2009/0281637 | A1* | 11/2009 | Martin | A61F 2/70 623/34 |
| 2010/0016990 | A1* | 1/2010 | Kurtz | A61F 2/58 623/24 |
| 2010/0141095 | A1* | 6/2010 | Park | H01L 41/1136 310/339 |
| 2011/0003279 | A1* | 1/2011 | Patel | G01D 7/00 435/5 |
| 2012/0143351 | A1* | 6/2012 | Tompkins | A61B 5/6828 623/34 |
| 2016/0015311 | A1* | 1/2016 | Jiang | A61B 5/6892 623/33 |
| 2018/0108525 | A1 | 4/2018 | Zhao et al. | |

OTHER PUBLICATIONS

Bai, Suo, et al. "High-performance integrated ZnO nanowire UV sensors on rigid and flexible substrates." Advanced Functional Materials 21.23 (2011): 4464-4469.

Brewster, Megan M., et al. "The growth and optical properties of ZnO nanowalls." The Journal of Physical Chemistry Letters 2.15 (2011): 1940-1945.

Chan, I-Hao, et al. "Deposition of Preferred-Orientation ZnO Films on the Lead-Free Ceramic Substrates and its Effects on the Properties of Surface Acoustic Wave Devices." Journal of the American Ceramic Society 95.7 (2012): 2254-2259.

Chang, Yi-Kuei, and Franklin Chau-Nan Hong. "The fabrication of ZnO nanowire field-effect transistors by roll-transfer printing." Nanotechnology 20.19 (2009): 195302.

Gao, S. Y., et al. "ZnO nanorods/plates on Si substrate grown by low-temperature hydrothermal reaction." Applied Surface Science 256.9 (2010): 2781-2785.

Greyson, Eric C., Yelizaveta Babayan, and Teri W. Odom. "Directed growth of ordered arrays of small-diameter ZnO nanowires." Advanced Materials 16.15 (2004): 1348-1352.

Han, Xi-Guang, et al. "Controlling morphologies and tuning the related properties of nano/microstructured ZnO crystallites." The Journal of Physical Chemistry C 113.2 (2008): 584-589.

Huang, Michael H., et al. "Catalytic growth of zinc oxide nanowires by vapor transport." Advanced Materials 13.2 (2001): 113-116.

Huang, Huihui, et al. "Seedless synthesis of layered ZnO nanowall networks on Al substrate for white light electroluminescence." Nanotechnology 24.31 (2013): 315203.

Islavath, Nanaji, et al. "Seed layer-assisted low temperature solution growth of 3D ZnO nanowall architecture for hybrid solar cells." Materials & Design 116 (2017): 219-226.

Iwu, Kingsley O., et al. "Enhanced quality, growth kinetics, and photocatalysis of ZnO nanowalls prepared by chemical bath deposition." Crystal Growth & Design 15.9 (2015): 4206-4212.

Jiao, Liying, et al. "Creation of nanostructures with poly (methyl methacrylate)-mediated nanotransfer printing." Journal of the American Chemical Society 130.38 (2008): 12612-12613.

Kumar, G. Mohan, et al. "Magnetic and optical property studies on controlled low-temperature fabricated one-dimensional Cr doped ZnO nanorods." CrystEngComm 12.6 (2010): 1887-1892.

Lee, Chul-Ho, et al. "Scalable network electrical devices using ZnO nanowalls." Nanotechnology 22.5 (2010): 055205.

Morin, Stephen A., and Song Jin. "Screw dislocation-driven epitaxial solution growth of ZnO nanowires seeded by dislocations in GaN substrates." Nano letters 10.9 (2010): 3459-3463.

Rafique, Subrina, Lu Han, and Hongping Zhao. "Density Controlled Growth of ZnO Nanowall-Nanowire 3D Networks." The Journal of Physical Chemistry C 119.21 (2015): 12023-12029.

Saravanakumar, Balasubramaniam, and Sang-Jae Kim. "Growth of 2D ZnO nanowall for energy harvesting application." The Journal of Physical Chemistry C 118.17 (2014): 8831-8836.

Tak, Youngjo, and Kijung Yong. "Controlled growth of well-aligned ZnO nanorod array using a novel solution method." The Journal of Physical Chemistry B 109.41 (2005): 19263-19269.

Tang, Jian-Fu, et al. "Controlled growth of ZnO nanoflowers on nanowall and nanorod networks via a hydrothermal method." CrystEngComm 17.3 (2015): 592-597.

Tseng, Zong-Liang, et al. "Electrical bistability in hybrid ZnO nanorod/polymethylmethacrylate heterostructures." Applied Physics Letters 97.21 (2010): 212103.

Tseng, Yung-Kuan, et al. "Two-step oxygen injection process for growing ZnO nanorods." Journal of materials Yesearch 18.12 (2003): 2837-2844.

Wan, Hong, and Harry E. Ruda. "A study of the growth mechanism of CVD-grown ZnO nanowires." Journal of Materials Science: Materials in Electronics 21.10 (2010): 1014-1019.

Wang, Xudong, Christopher J. Summers, and Zhong Lin Wang. "Large-scale hexagonal-patterned growth of aligned ZnO nanorods for nano-optoelectronics and nanosensor arrays." Nano letters 4.3 (2004): 423-426.

Wang, Mingsong, et al. "Low-temperature solution growth of high-quality ZnO thin films and solvent-dependent film texture." The Journal of Physical Chemistry C 112.6 (2008): 1920-1924.

Wang, Jian, et al. "A highly sensitive H 2 O 2 sensor based on zinc oxide nanorod arrays film sensing interface." Analyst 135.8 (2010): 1992-1996.

Water, Walter, and Shih-En Chen. "Using ZnO nanorods to enhance sensitivity of liquid sensor." Sensors and Actuators B: Chemical 136.2 (2009): 371-375.

Xu, Feng, and Litao Sun. "Solution-derived ZnO nanostructures for photoanodes of dye-sensitized solar cells." Energy & Environmental Science 4.3 (2011): 818-841.

Zhang, Hui, et al. "Controllable growth of ZnO microcrystals by a capping-molecule-assisted hydrothermal process." Crystal growth & design 5.2 (2005): 547-550.

* cited by examiner

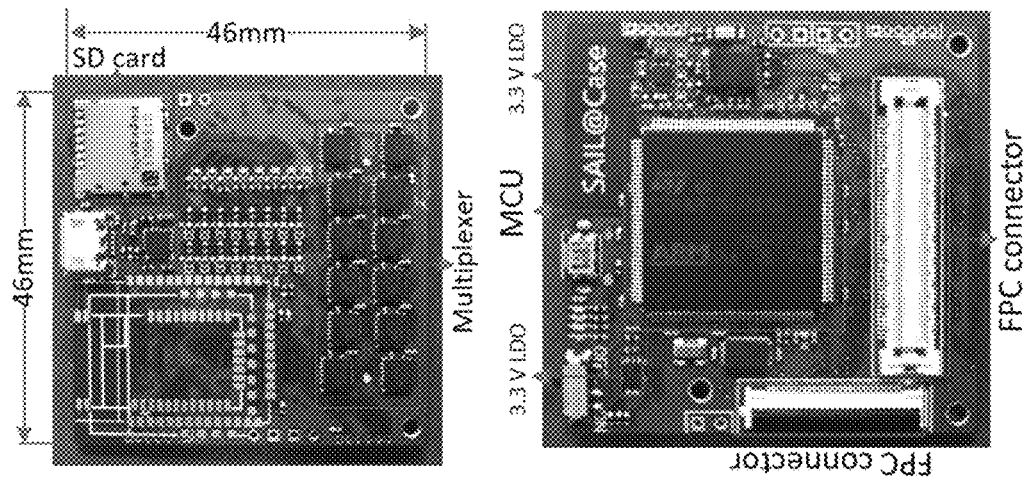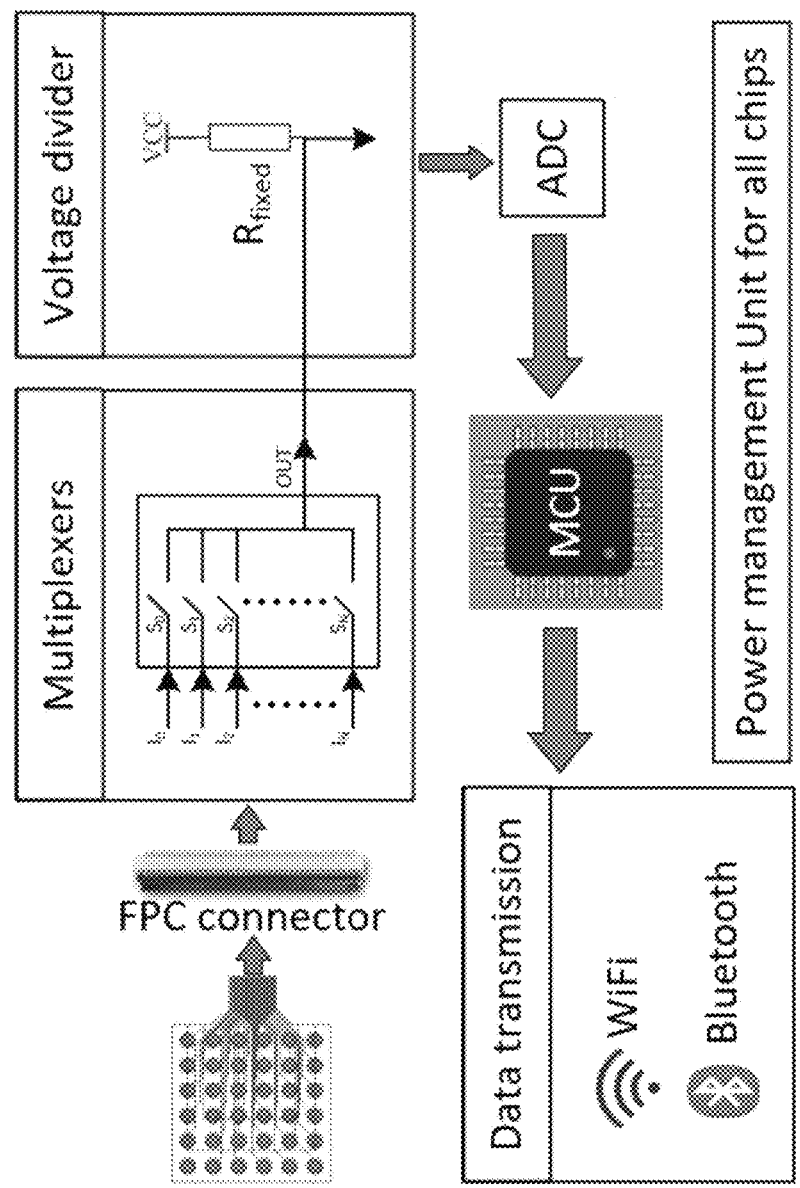
FIG. 12

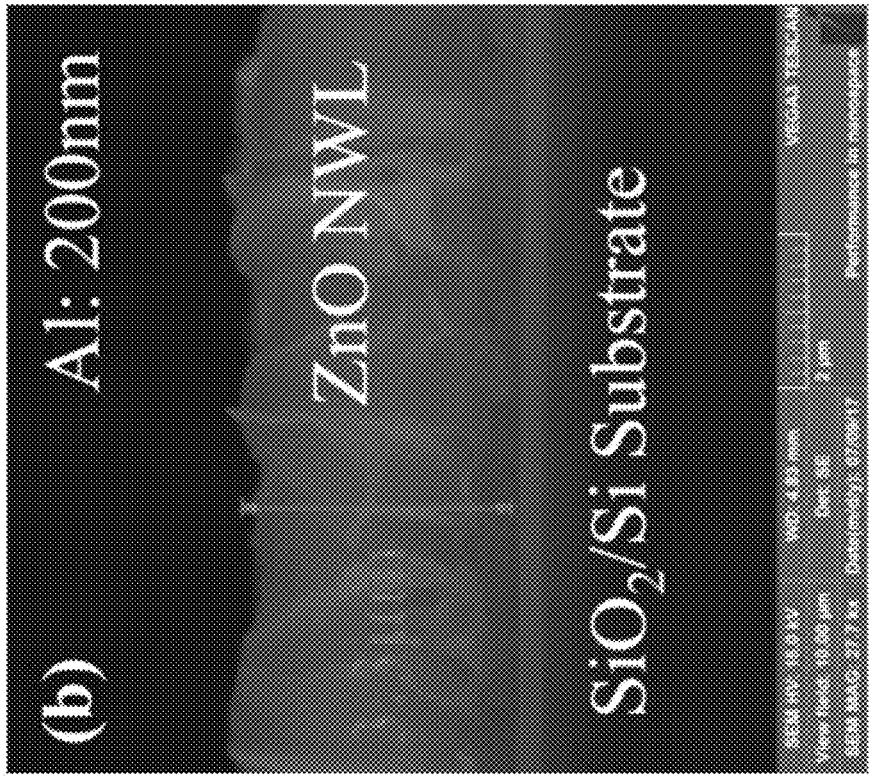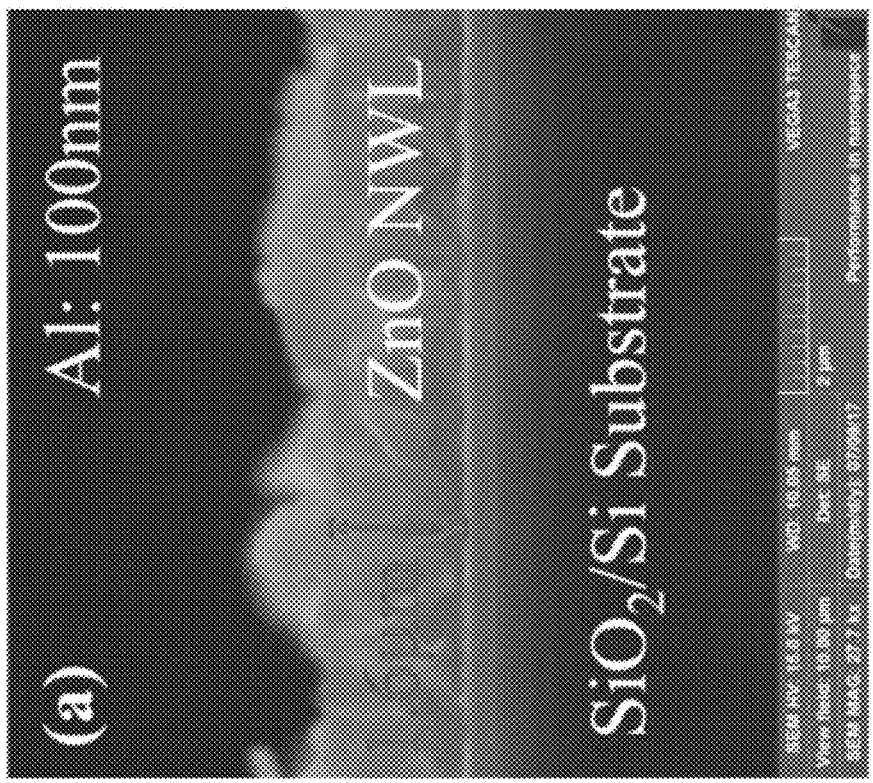
FIG. 18

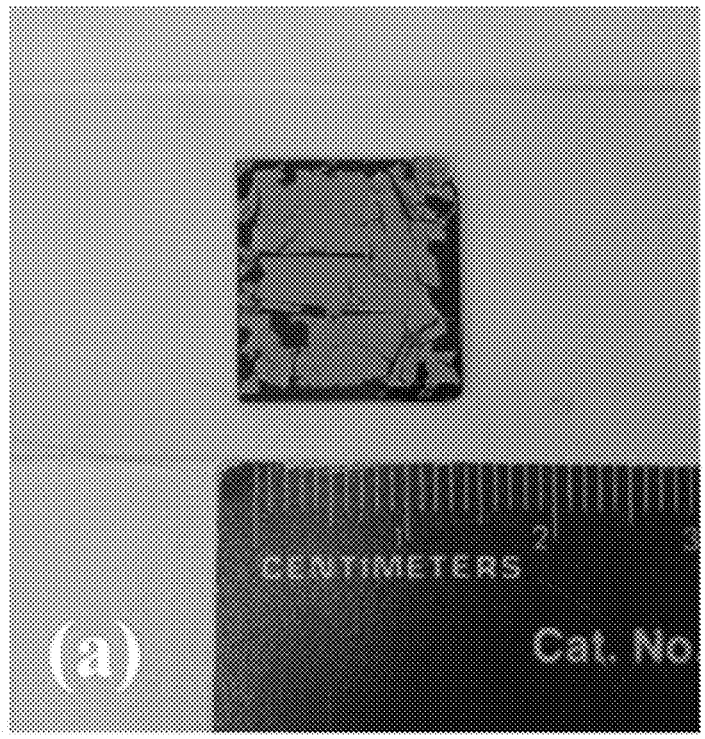
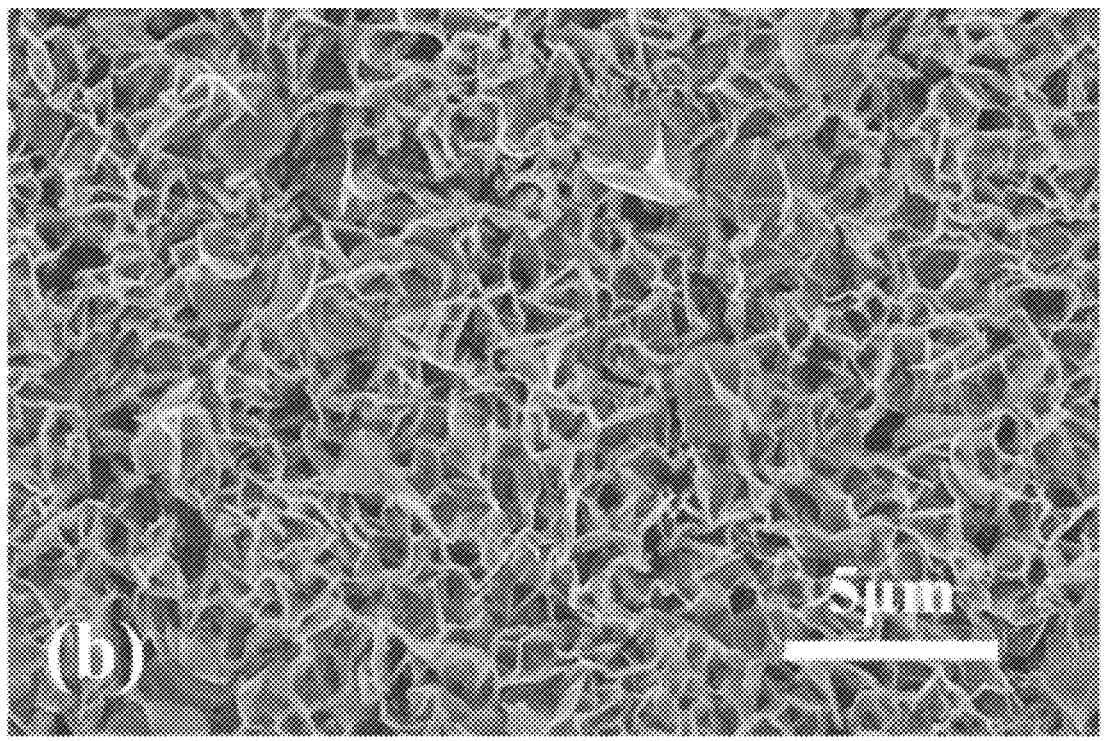
FIG. 22

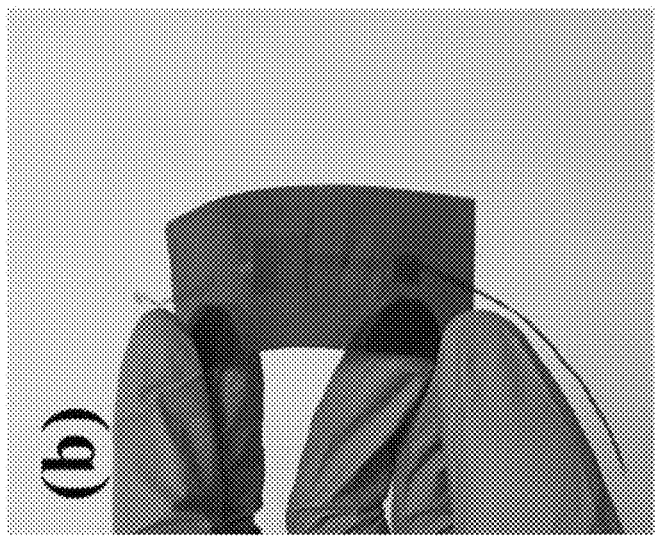
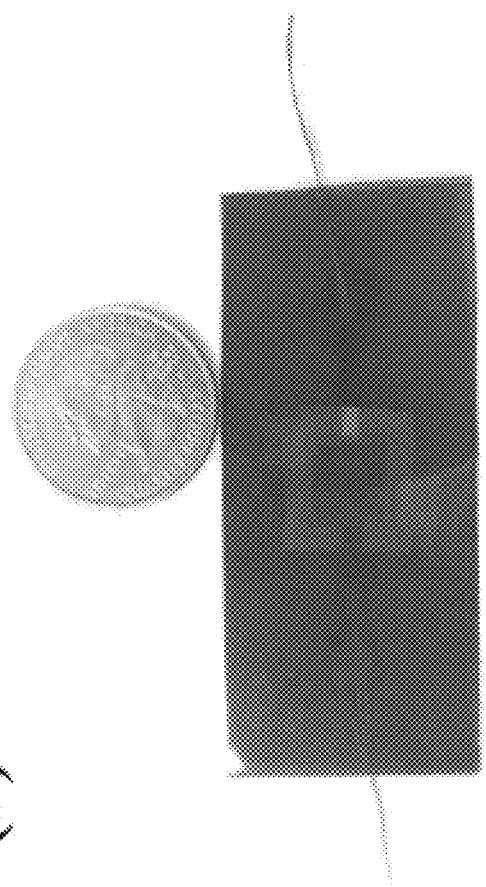
FIG. 23

INTELLIGENT PROSTHETIC SOCKET

CROSS-REFERENCE TO RELATED APPLICATION

This application claims the benefit of U.S. Provisional Application Ser. No. 62/654,775, filed Apr. 9, 2018, entitled "WEARABLE NANOFABRICATION DESIGNS CREATE BETTER FITTING INTELLIGENT PROSTHETIC SOCKETS", the entirety of which is hereby incorporated by reference for all purposes.

GOVERNMENT FUNDING

This invention was made with government support under CNS-1664368 awarded by National Science Foundation. The government has certain rights in the invention.

TECHNICAL FIELD

This disclosure generally relates to prosthetic devices and, more specifically, to an intelligent socket for a prosthetic device with an inner-socket sensor array to record real-time pressure and/or shear force data within the socket.

BACKGROUND

Amputations, particularly of the lower limb due to vascular disease, infection, tumor, trauma, and/or diabetes, are a worldwide problem. To increase normalcy after lower limb amputation, a patient can use a prosthetic device to replace the amputated leg. Generally, the prosthetic device includes a socket that interfaces with the remaining residual limb. The socket can be fitted to the remaining residual limb, but changes in body weight and the size of the residual limb can result in a socket that no longer fits perfectly. A poorly-fitting socket can lead to chronic skin problems, including pressure ulcers, dermatitis, infections, and pain, which seriously affect a patient's health and quality of life. However, making a socket that fits well over the long term is a complicated and challenging process. Currently, a liner is used to provide a vacuum seal and cushioning materials. Although the liner can help prolong the comfort associated with the socket, the liner does not monitor the occurrence of chronic skin problems associated with a poorly fitting socket.

SUMMARY

The present disclosure overcomes the challenges of making a socket that fits well over the long term by equipping an intelligent socket with an inner-socket sensor array to record real-time pressure and/or shear force data within the socket.

In an aspect, a system that can record real-time pressure and/or shear force data within a socket for a prosthetic device is described. The system includes the socket that is designed to fit a patient's residual limb. The system also includes a sensor array that can be configured to be placed within the socket to detect pressure and/or shear force on the patient's residual limb. The sensor array includes a piezo-electric material and a uniform distribution of a plurality of metal pads on either side of the piezo-electric material. Each of the plurality of metal pads on either side of the piezo-electric material includes at least one wire connected to a common port.

In another aspect, a method for providing a visualization of pressure and/or shear force within a socket for a prosthetic device is described. A sensor array within a socket for a prosthetic device continuously detects pressure and/or shear force experienced by a patient's residual limb inside the socket. A connector associated with the sensor array sends data related to the pressure and/or shear force to a signal processing circuit. The signal processing circuit processes the data related to the pressure and/or shear force and sends the processed data related to the pressure and/or shear force to a computing device. A processor associated with the computing device provides a visualization of at least one of the pressure and the shear force. A visualization device associated with the computing device displays the visualization in a user perceivable manner.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 12 illustrates the design of a signal processing circuit (architecture and prototype).

FIG. 18 shows cross-sectional SEM on ZnO NWLs grown at 80 degrees Celsius on a $SiO_2$/Si substrate with ZNH:HMT molar ratio of 1:1 using different Al film thicknesses.

FIG. 22 shows transferred ZnO NWLs on SI substrate, including a photographic image and a top view SEM image of the film.

FIG. 23 shows photograph images of the ZnO NWL test device and bending of the ZnO test device.

DETAILED DESCRIPTION

This disclosure describes an intelligent socket for a prosthetic device with an inner-socket sensor array to record real-time pressure (e.g., pressure distribution) and/or shear force data within the socket. For example, the pressure and/or shear force data relate to the pressure and/or shear force experienced by a patient when the patient's residual limb (or "stump") is within the socket. A liner can also be used in connection with the intelligent socket for patient comfort and/or to increase patient comfort and/or aid in the determination of real-time pressure and/or shear force. For example, an electrically responsive material can be placed around an elastomeric liner to help to monitor pressure and/or shear force experienced by the patient's stump within the socket. Additionally, the liner can be made of an electrically active material, which can change its shape under low electric current. The low electric current can come from a controller to adjust and redistribute pressure and shear force over the entire residual limb.

The pressure and/or shear force data can be factors that indicate a poor fitting socket, which can lead to skin conditions pressure ulcers, dermatitis, infections, and pain. The real-time pressure and/or shear force data can be used to adjust the socket's fitting to minimize the pressure and/or shear force. Additionally, the pressure and/or shear force data with time can be dynamically visualized by a user and/or medical professional (e.g., on a computing device, such as a desktop computer, a laptop computer, a tablet computer, a mobile computing device, or the like). The term "user" is synonymous with the terms "subject" and "patient" and refers to a bipedal animal, like a human. For example, the user can be an amputee making use of the intelligent socket. The term "real time" can refer to the actual time during which a process or event occurs (e.g., the sensor array can sense pressure and/or shear force values, the values can be processed, and a visualization can be updated virtually immediately with little or no delay). The term "continuously" can refer to a repeated event without exception (e.g., the pressure and/or shear force can be recorded periodically at a set interval that is unchanging when the stump is within the socket). As such the pressure and/or shear force data can be detected continuously and in real time.

Figure 1:
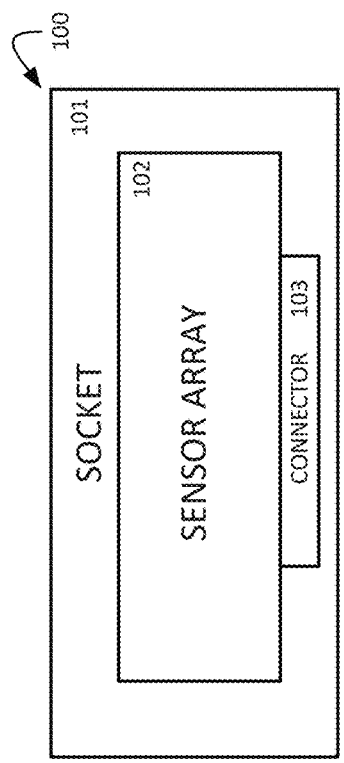
FIG. 1 illustrates an intelligent socket for a prosthetic device with an inner-socket sensor array to record real-time pressure and/or shear force data.

FIG. 1 illustrates an intelligent socket 100 for a prosthetic device. The intelligent socket 100 can include a socket 101 for the prosthetic device. The socket 101 can be preconfigured to be customized for a particular patient so that the socket 101 fits the patient's stump. Over time, however, the socket 101 may no longer be customized for the patient. This can occur for various reasons, such as variation in body weight, edema, or the like. Accordingly, the intelligent socket 100 includes an inner-socket sensor array 102 to detect pressure (e.g., pressure distribution) and/or shear force values within the socket 101 when the patient's stump is within the socket 101. The inner socket sensor array 102 is in communication with a connector 103 to collect and transmit the pressure and/or shear force data detected by the inner-socket sensor array 102. It should be noted that the inner-socket sensor array 102 can be customized to different sizes based on the size of the socket 101 (as described in PCT Application No. PCT/US2019/021637, entitled "CUSTOMIZABLE PRESSURE SENSOR ARRAY", which is incorporated herein by reference in its entirety).

In some instances, the patient may wear a liner device over the stump to separate the stump from the socket 101. The liner device may aid in the detection of pressure and/or shear force. For example, the liner device may include one or more electrically-active polymers EAPs) that can change conformational shape in response to current. The change in shape can redistribute the forces to minimize areas of high stress and shear, thereby reducing the risk of pressure ulcers and skin breakdown. The prosthetic liner may also include a material that helps to increase comfort. For example, the prosthetic liner can have moisture-wicking abilities and/or provide mechanical support to increase comfort. Accordingly, the prosthetic liner can include materials like elastomer-hydrogel blends, e.g., urethane-hydrogel nanotubes in porous polymers.

Figure 2:
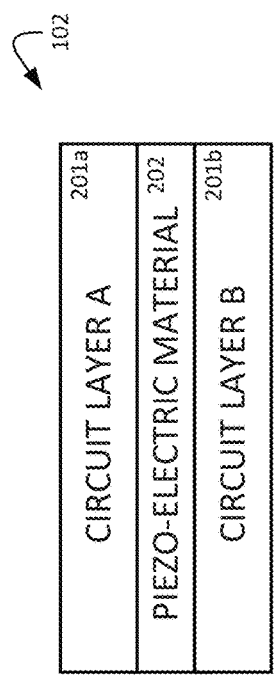
FIG. 2 illustrates an example layout of the sensor array shown in FIG. 1.

An example configuration of the sensor array 102 is shown in FIG. 2. In its simplest form, the sensor array 102 can include a piezo-electric material 202 and one or more circuit layers (circuit layer A 201a and/or circuit layer B 201b, as illustrated). The piezo-electric material 202 can be sensitive to pressure and/or shear force. Examples of such a piezo-electric material 202 that can convert a mechanical signal to an electrical signal are zinc oxide (e.g., zinc oxide nanowall networks), gallium oxide (e.g., epsilon phase gallium oxide), and the like. The piezo-electric material 202 can also be flexible and easily cut, like a fabric, a thin sheet, or the like.

The one or more circuit layers are represented as circuit layer A 201a and circuit layer B 201b, which sandwich the piezo-electric material 202. However, the piezo-electric material 202 may be contacted by only one of circuit layer A 201a and circuit layer B 201b. For example, circuit layer A 201a may be sandwiched by the piezo-electric material 202 and circuit layer B 201b. In another example, circuit layer B 201b can be sandwiched by circuit layer A 201a and the piezo-electric material 202. In still another example, circuit layer A 201a and circuit layer B 201b can be next to one another and each contacting the piezo-electric material 202. Circuit layer A 201a and/or circuit layer B 201b can be placed in numerous other arrangements with the piezo-electric material 202. One of the circuit layers (e.g., circuit layer A 201a) can connect the piezo-electric material 202 to a source voltage via a fixed resistance, while the other of the circuit layers (e.g., circuit layer B 201b) can connect the piezo-electric material 202 to a ground electronic level.

Each of the one or more circuit layers (e.g., circuit layer A 201a and/or circuit layer B) can include a uniform distribution of a plurality of flexible circuits. The one or more circuit layers (e.g., circuit layer A 201a and/or circuit layer B) can be individually flexible to create a plurality of flexible circuits that are wired to a common connector (or port) 103. As an example, the one or more circuit layers can include one or more electrical components deposited onto flexible substrates (e.g., as a flexible printed circuit board or PCB). The one or more electrical components can include pads (e.g., copper pads) and wires. The wires can connect the pads to the common connector 103.

Figure 3:
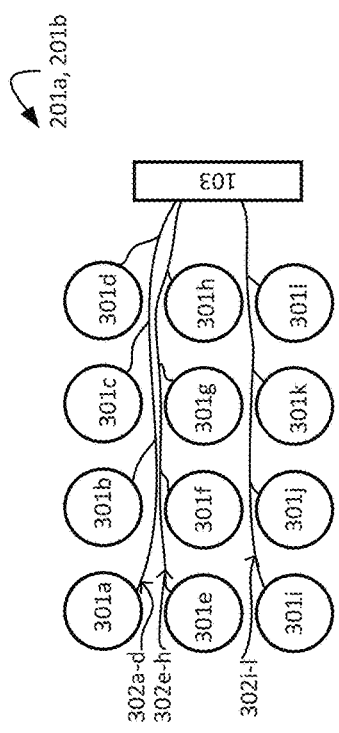
FIG. 3 illustrates an example of the copper pads and wiring of circuit layer A and/or circuit layer B in FIG. 2.

FIG. 3 is an example of circuit layer A 201a and/or circuit layer B 201b, which each include an equal number of uniformly distributed pads 301a-l. Circuit layer A 201a and/or circuit layer B 201B can include a plurality of pads (representing electrical components) 301a-l. Twelve pads are shown in FIG. 3, but this number is not limiting and is instead only exemplary. Each of the pads 301a-l is connected to at least one wire 302a-l (each of 302a-l is shown as a single wire, but may each represent a plurality of wires). The wires 302 a-l can be positioned relative to the respective flexible circuit (or pad) 301 a-l to ensure that each of the plurality of flexible circuits 301 a-l is connected to the common connector 103, even when customized so that every one of the plurality of plurality of flexible circuits 301 a-l remaining on the customized pressure sensor array as full flexible circuits and partial flexible circuits is still usable after the pressure sensor array is customized. Notably, the pressure sensor array retains its original sensing resolution after being customized to any number of different sizes due to the uniform distribution of flexible circuits on the one or more circuit layers (e.g., circuit layer A 201a and/or circuit layer B). As an example, each wire 302a-l can be connected to an internal portion of the respective flexible circuit (internal meaning away from or opposite to an edge of the socket 101). The wires 302a-l connect the pads 301a-l to the common connector 103 and transmit data from the pads 301a-l to the common connector 103, which can connect through a wired and/or wireless communication link to signal processing circuitry (shown, for example, in FIGS. 4 and 5).

Figure 4:
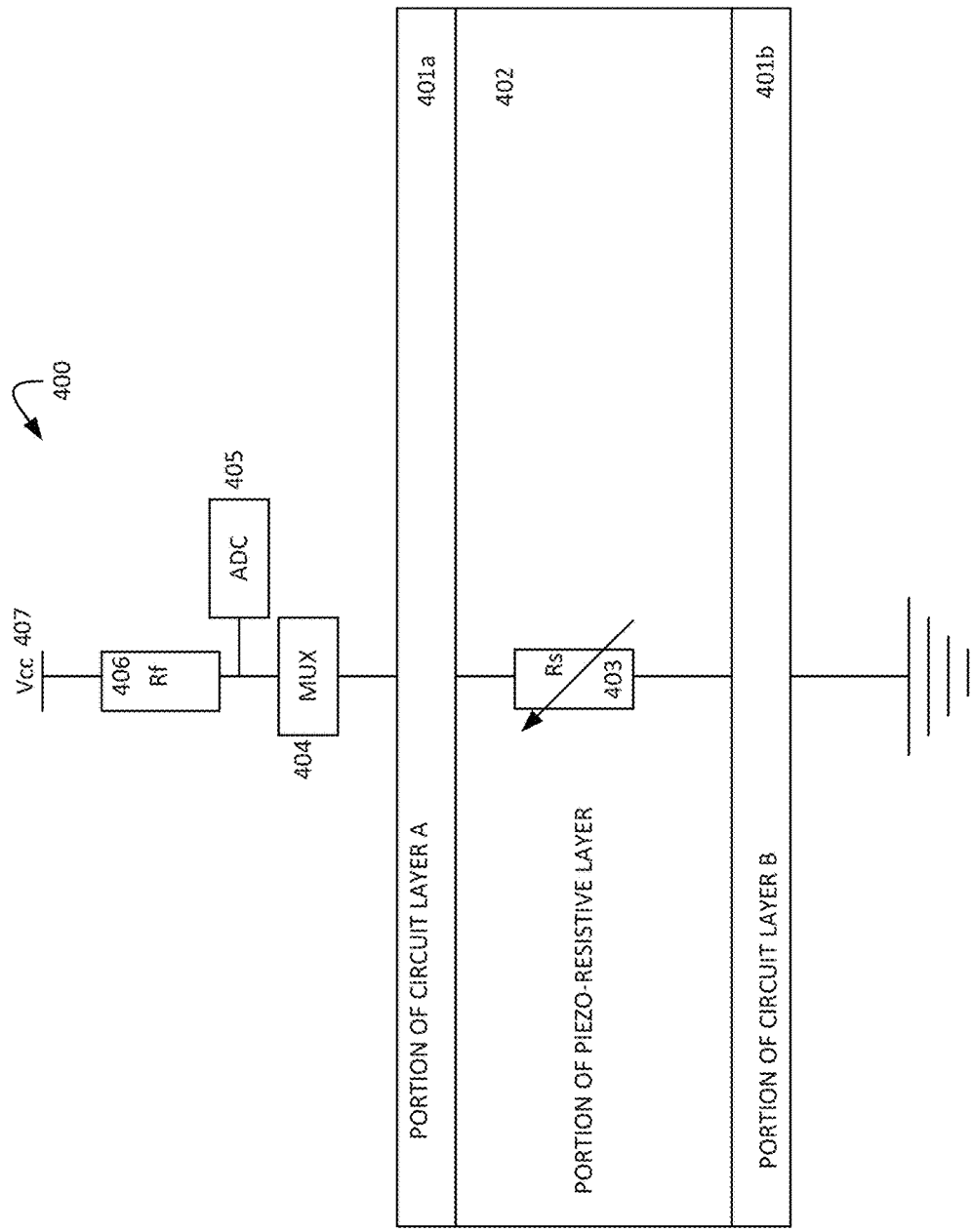
FIG. 4 illustrates an example the mechanism for determining a resistance of a sensor of the sensor array of FIG. 1.

FIG. 4 illustrates an example of data transmission from a single sensor (with the piezo-electric material being a piezo-resistive layer 302 in this example) to signal processing circuitry. The signal processing circuitry (as shown in FIG. 4, including multiplexer 404, analog-to-digital convertor 405, and a voltage divider circuit 406, 407, for example) can receive signals from each of the wires 302a-l and from each of circuit layer A 201a and circuit layer B 201b and determine the resistance of the piezo-resistive layer between portions of circuit layer A 201a and circuit layer B. Based on the resistance, the signal processing circuitry can determine the pressure experienced by the different portions of the piezo-resistive layer 202. The signal processing circuit can receive many inputs from many individual circuits. FIG. 4 shows a single circuit 400 (a circuit in this sense is a portion of circuit layer A 401a (or a pad), a portion of circuit layer B 401b (or a pad opposed to the pad in circuit layer A 401a), and a portion of the piezo-resistive layer 402. The piezo-resistive material within the piezo-resistive layer 402 can be modeled as a variable resistance (Rs 403) that can vary in a manner proportional (or otherwise related) to the pressure applied to the piezo-resistive material.

A portion of circuit layer B 401b can connect the portion of the piezo-resistive material 402 to the ground electronic level. A portion of circuit layer A 401a can connect the portion of the piezo-resistive material 402 to a source voltage (Vcc 406) via a fixed resistor (Rf 407). A voltage divider circuit (represented by Vcc 406, Rf 407, and MUX 404, but may include additional components) and an analog to digital convertor (ADC 405) can be used to measure the voltage drop on the pressure sensor. The resistance of the individual sensor can be measured with the following Equation:

$$Rsensor = \frac{Vsensor\ Rfixed}{Vcc - Vsensor},$$

where Rsensor is the resistance of the portion of piezo-resistive material 402 (represented as Rs 403 in FIG. 4), Rfixed (represented as Rf 407 in FIG. 4) is the resistance of the fixed resistor that is used to build the voltage divider circuit, Vsensor is the voltage drop on the sensor, which could be measured by ADC 405, and Vcc 407 is the source voltage, By controlling the MUX 404, all pressure sensors in the array can be scanned and a pressure map can be acquired.

Figure 5:
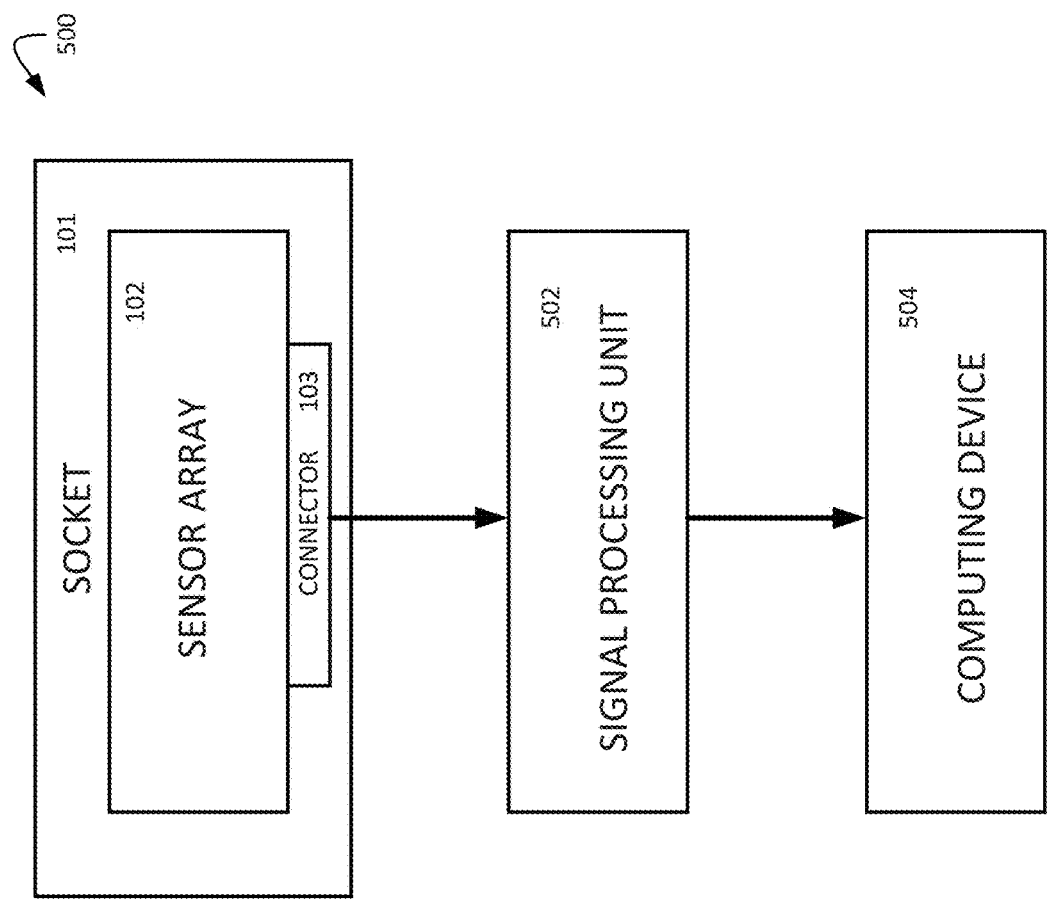
FIG. 5 illustrates an example of a system that can monitor the real-time pressure and/or shear force data inside a socket of a prosthetic device.

FIG. 5 shows an example system 500 that can monitor the real-time pressure and/or shear force data inside a socket 101 of a prosthetic device. As described above, a sensor array 102 and connector 103 can be fit within the socket 101 to record the real-time pressure and/or shear force data. In some instances, the patient may wear a liner device over the stump to separate the stump from the socket 101, as described above. The connector 103 can transmit the pressure and/or shear force data to the signal processing unit 502 (also referred to as signal processing circuit) over a wired connection and/or a wireless connection. The signal processing unit 502 can include one or more of a multiplexer, a voltage divider circuit, an analog-to-digital convertor, a control unit, a power management unit, and a data transmission unit. The signal processing unit 502 can process the pressure and/or shear force data and send the pressure and/or shear force data to a computing device (e.g., a mobile computing device, like a tablet computer, a smartphone, or the like, but my also be a desktop computing device, a laptop computing device, or the like), which can put the data into a visualization. The computing device can be linked to or include a visualization device to display a visualization of the pressure and/or shear force data in a human-comprehensible form. For example, the visualization can be a pressure map showing areas where the greatest pressure is exerted. The wireless data transmission can be over a WiFi network, but can also be over a short-range network, like Bluetooth or Bluetooth Low Energy.

Figure 6:
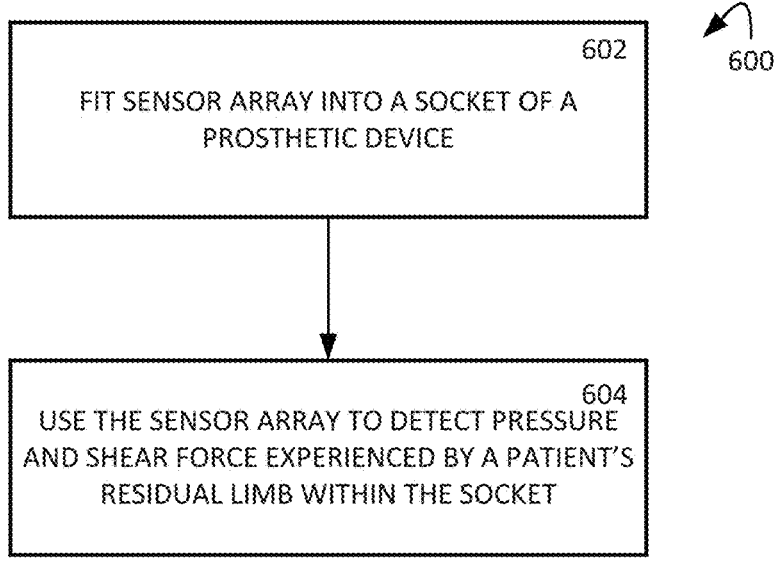
FIG. 6 illustrates a method for using a sensor array in a socket for a prosthetic device to record real-time pressure and/or shear force data.
Figure 7:
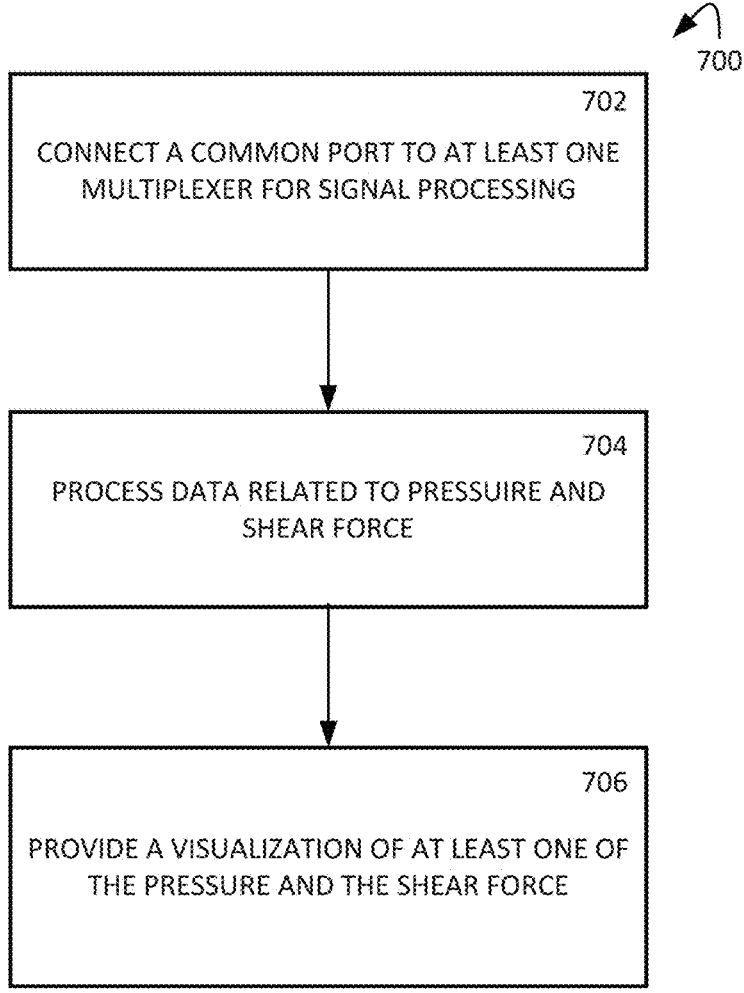
FIG. 7 illustrates a method for monitoring pressure and/or shear force experienced within a socket of a prosthetic device.

In view of the foregoing structural and functional features described above, example methods that can be performed by one or more elements of the system 500 will be better appreciated with reference to FIGS. 6-7. While, for the purposes of simplicity of explanation, the example methods of FIGS. 6-7 are shown and described as executing serially, the present examples are not limited by the illustrated order, as some actions could in other examples occur in different orders or concurrently from that shown and described herein. Moreover, it is not necessary that all described actions be performed to implement a method. One or more aspects of the methods can be stored in one or more non-transitory computer-readable media and executed by one or more processing resources, such as described herein.

FIG. 6 illustrates a method 600 for using a sensor array in a socket for a prosthetic device (An example of the sensor array in the socket is shown in FIG. 1) to record real-time pressure and shear force data (however, it will be noted that instances exist where the sensor array may record pressure or shear force data). At 602, a sensor array (e.g., sensor array 102) can be fit into a socket of a prosthetic device (e.g., socket 101). In some instances, the sensor array can be scaled based on the size of the socket without losing sensing ability (e.g., resolution). At 604, the sensor array can be used to detect pressure and/or shear force experienced by a patient's residual limb within the socket. The pressure and/or shear force can be examined over time to customize the socket for the individual patient.

FIG. 7 illustrates a method 700 for monitoring pressure and/or shear force experienced within a socket of a prosthetic device. The method 700 can be performed, for example, by the system 500 shown in FIG. 5. At 702, a common port (e.g., connector 103) can be connected to at least one multiplexer 404 (or other component of the signal processing unit 502) for signal processing. At 704, data related to pressure and/or shear force can be processed (e.g., by components of the signal processing unit 502 or the computing device 504). At 706, a visualization of at least one of the pressure and the shear force can be provided (e.g., by the computing device 504 to a visualization device associated with the computing device 504). In some instances, the visualization can be displayed on a model of the stump. Based on the visualization, the pressure and/or shear force can be redistributed (e.g., by altering a configuration of a liner worn by the patient). The configuration can be altered by applying a small current to the linear so that the confirmation of the liner changes.

EXPERIMENTAL

Experiment 1

Figure 8:
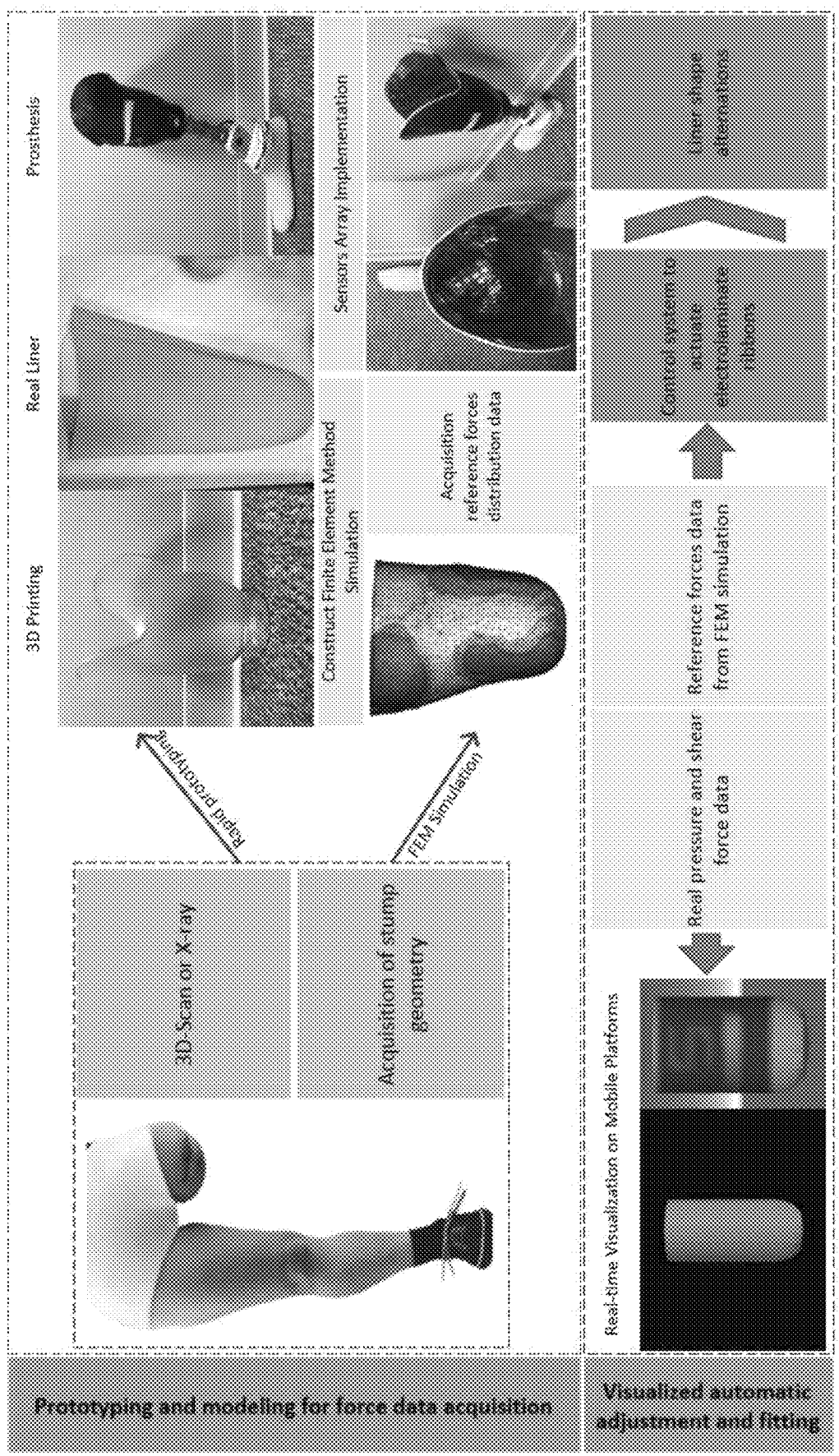
FIG. 8 illustrates an example of a smart prosthesis system.
Figure 9:
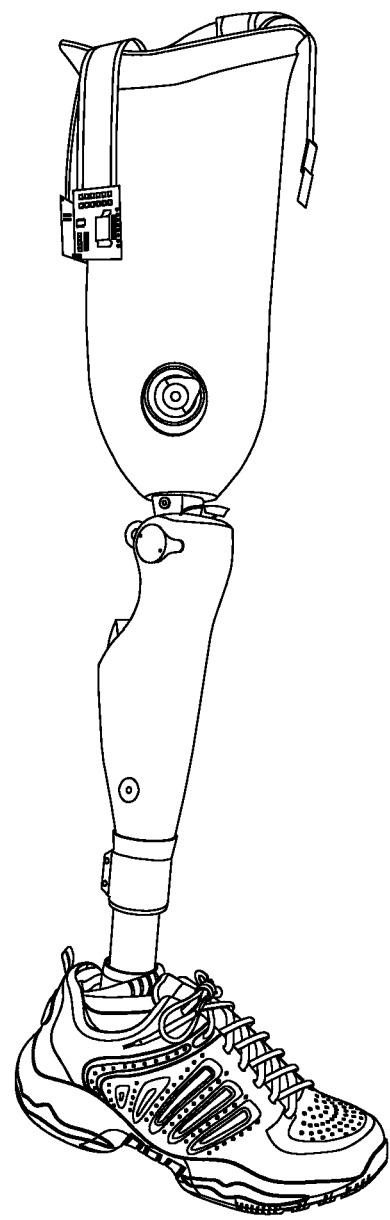
FIG. 9 illustrates an example of a prosthetic leg that can be used in the smart prosthesis system of FIG. 8.

The following experiment shows the design and use of a smart prosthesis system with an in-socket customizable sensor array to record real-time pressure and/or shear force data. FIG. 8 shows a design of the smart prosthesis system with the overall system divided into two stages according to its functions: (1) prototyping and modeling for force data acquisition (top of FIG. 8) and (2) visualized automatic adjustment and fitting (bottom of FIG. 8). FIG. 9 shows an example of a prosthetic leg that can be used in connection with the smart prosthesis system of FIG. 8. Notably, the sensor array, lining, and the entire adjustable socket system is flexible, cloth-like, and confluent.

Customizable Pressure Prosthesis Socket

An amputee above the knee (the subject) was fitted for a customized socket for a prosthetic leg by considering the geometry of the residual limb. The geometry was acquired through 3D-scanning and/or X-ray. The geometry information was fed into a FEA (finite element analysis) model for force distribution stimulation. The FEA model was established based on the actual shapes of the socket, the residual limb surface, and the internal bones of the subject. All materials were assumed to be isotropic, homogeneous, and linearly elastic in the stimulation. The Poisson ratio was assumed to be 0.49 for soft tissues, 0.3 for bones, and 0.39 for prosthetic liner, while the Young's modulus was assumed to be 200 kPa for soft tissues, 10 GPa for bones, and 380 kPa for prosthetic liner. The customized socket was chosen to be the shape that provided a minimal force distribution. The customized socket was rapidly prototyped using 3D printing. A customizable pressure sensor array was placed within the customized socket (individual sensors within the customizable pressure sensor array could collect real-time pressure and/or shear-force data from the stump-socket interface).

A prosthetic liner was worn by the subject to cover the stump when placed in the socket. In some instances, the prosthetic liner can include one or more electrically active polymers (EAPs), such as electrolaminates, that can change conformational shape in response to current (e.g., a low electric current). The change in shape can redistribute the forces to minimize areas of high stress and shear, thereby reducing the risk of pressure ulcers and skin breakdown. The prosthetic liner may also include a material that helps to increase comfort. For example, the prosthetic liner can have moisture-wicking abilities and/or provide mechanical support to increase comfort. Accordingly, the prosthetic liner can include materials like elastomer-hydrogel blends, e.g., urethane-hydrogel nanotubes in porous polymers.

Based on recordings from the pressure sensor array, the pressure distribution and calculated shear forces can be mapped. The maps can be displayed over a model, and the pressure and shear forces can be redistributed in real-time to prevent the development of skin conditions. A control system can be employed for segmental adjustment based on the pressure and shear forces.

Customizable Pressure Sensor Array

The customizable pressure sensor array can be a cloth-like flexible sensor array (e.g., a pressure sensor array) with sensors evenly distributed throughout the socket in a square-shaped array. The array can be trimmed to different sizes without losing sensing ability (described in PCT/US2019/021637, which is incorporated herein by reference). It should be noted that the design can support as many pressure sensors as necessary to cover the socket (e.g., 36 sensors, 96 sensors, greater than 500 sensors, etc.). It should also be noted that all circuit wires in the customizable pressure sensor array go toward the middle of the customizable pressure sensor array to ensure that all of the pressure sensors remaining on the customizable array after trimming would be connected with a flexible printed circuit (FPC) connector.

Figure 10:
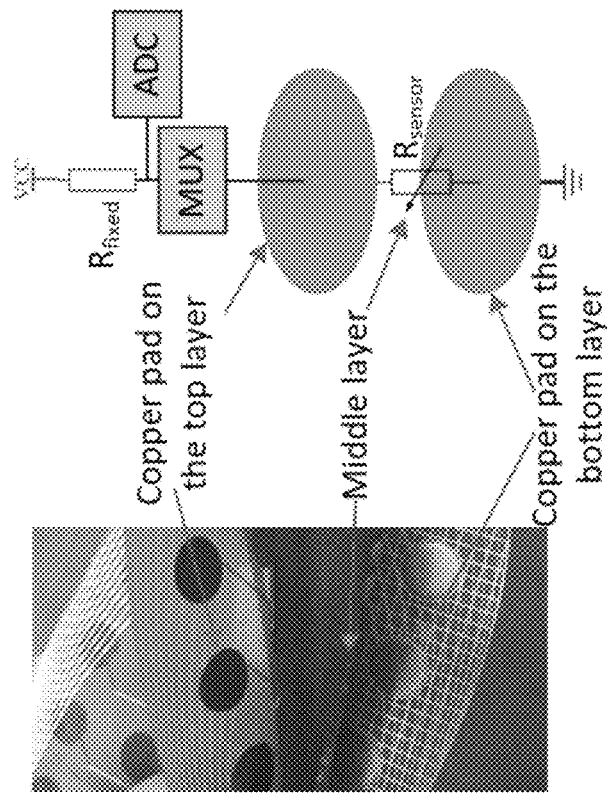

A three-layered structure of the customizable pressure sensor array is shown in FIG. 10 (left). The top and bottom layers included copper pads. The middle layer included a piezo-resistive material that is a commercially available (from EeonTex™), thin (0.8 mm thickness), light weight (170 g/m$^2$), trimmable, and flexible fabric. Each of the thirty six discrete pressure sensors included a pair of copper pads (one from the top layer and one from the bottom layer) with the piezo-resistive material in between.

Figure 11:
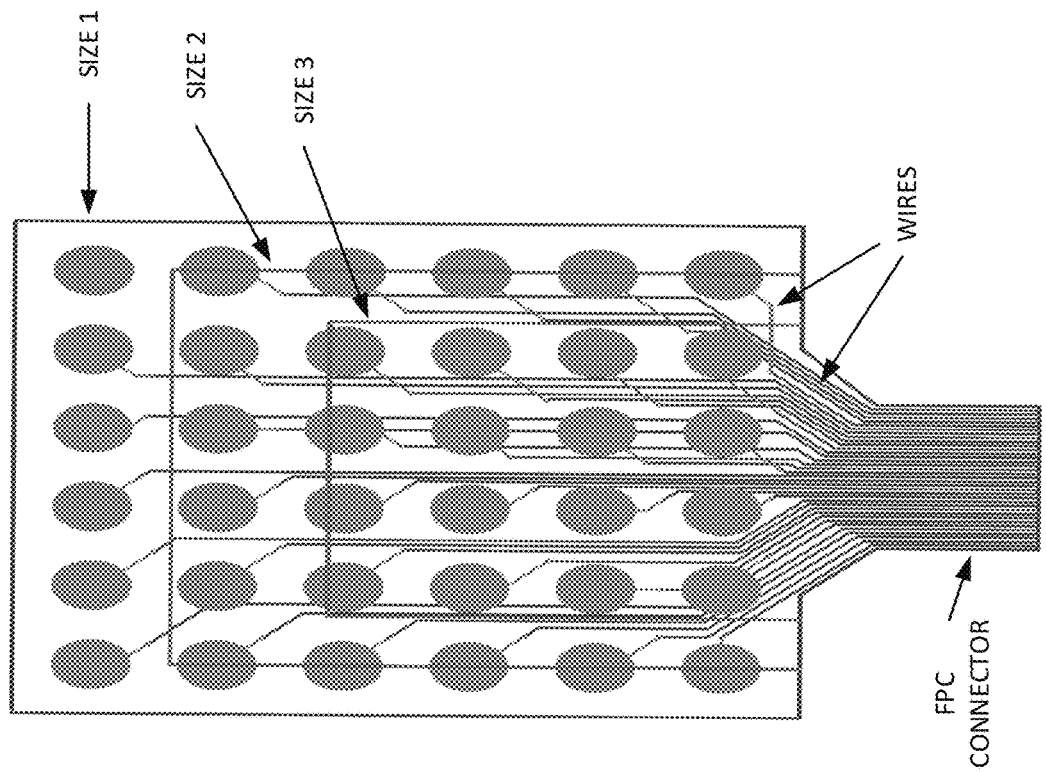
FIGS. 10 and 11 illustrate the mechanism of the piezo-resistive pressure sensor array.

A model of a single pressure sensor is shown in FIG. 10 (right), with a variable resistor representing the middle layer because the resistance of the piezo-resistive material varies with applied pressure. The copper pad on the bottom layer connected the piezo-resistive material to the ground, and the copper pad on the top layer connected the piezo-resistive material to the source voltage via a fixed resistor. The pressure sensor array is scalable to different sizes without losing sensing resolution, as shown in FIG. 11.

Signal Processing Circuit

A FPC connector was used to connect the customizable pressure sensor array to a signal processing circuit (shown in FIG. 12), which included multiplexers that connect the pressure sensors to a voltage divider circuit and analog-to-digital convertor (ADC).

Data measured by the sensors was transmitted through wireless data transmission units (WiFi and Bluetooth) and/or stored on the attached memory card. A power management unit was used to supply suitable power to all of the components. A micro-controller unit (MCU) was used to control a work state of all of the function modules.

Testing Pressure of the Prosthesis Socket

The customizable pressure sensor array was placed within a plain lower extremity prosthetic socket (configured for above knee amputation). Forces were applied artificially (1) using two fingers on a side of the socket at different locations (shown in FIG. 13, top of elements (a), (b), and (c)) and (2) using a palm (shown in FIG. 13, top of element (d)).

Figure 13:
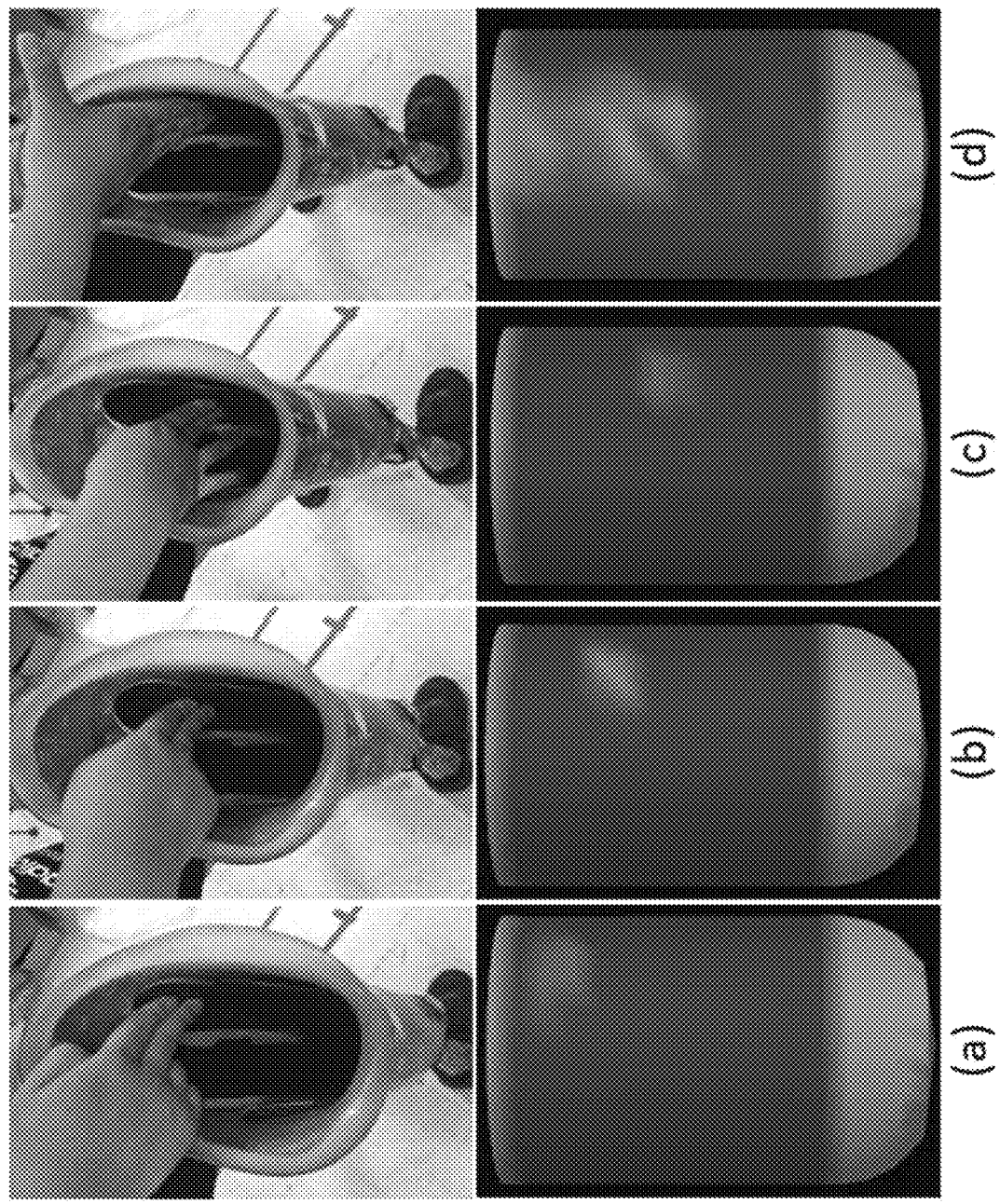
FIG. 13 illustrates inner-prosthesis sensor array evaluation with corresponding pressure mapping visualizations.

Pressure data was recorded for each applied force and represented as pressure map. The pressure maps corresponding to the force applied using two fingers on the side of the socket at different locations are shown in FIG. 13, bottom of elements (a), (b), and (c). The pressure map corresponding to the force applied using the palm is shown in FIG. 13, bottom of element (d). The pressure maps illustrate that the pressure change is larger with the palm than the fingers.

Pressure Maps

The pressure maps were created by mapping each sensor to a corresponding vertex of model mesh and saving the relationship. Markers were applied to ensure that sensor and vertex locations on the limb are the same as the model. The vertex index and matched sensor index were saved in a matrix. The pressure data was shown by a color map. Pressure map visualization on various mobile platforms (e.g., Android, iOS, Hololens, etc.) was shown. This visualization can help patients and medical providers monitor the prostheses for abnormal force distribution changes. At present, the customizable sensor array and its supporting hardware circuit are designed and prototyped.

Experiment 2

The following experiment shows the synthesis of ZnO nanowall (ZnO NWL) networks on various substrates using a hydrothermal process with an aluminum seed layer. The ZnO NWL networks provide a flexible piezoelectric material, which can be used as the piezo-electric layer within the in-socket customizable sensor array described above to record real-time pressure and/or shear force data.

Synthesis of ZnO NWLs

Figure 14:
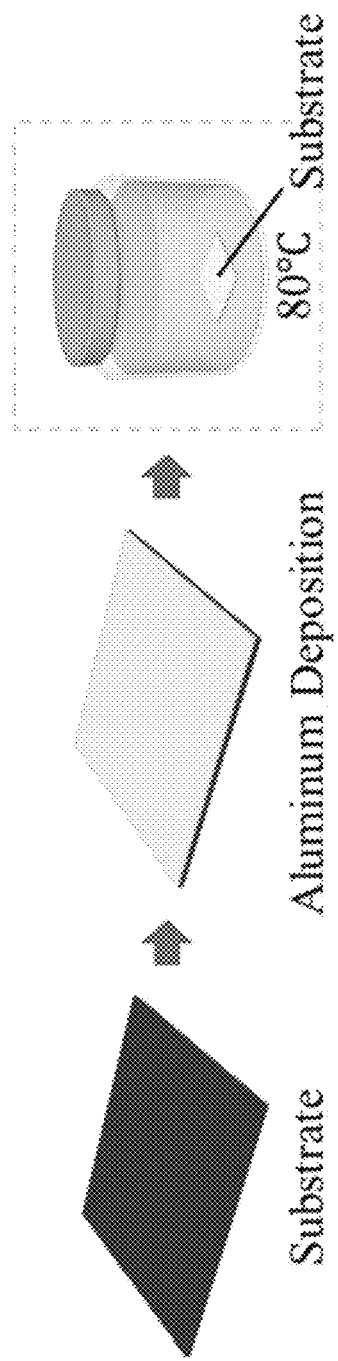
FIG. 14 is a schematic diagram of the setup for ZnO nanowall (NWL) hydrothermal synthesis.

FIG. 14 shows a schematic of the ZnO NWLs growth procedure. $SiO_2$-on-Si, Si, polyimide (PI) and polyethylene terephthalate (PET) were used as the growth substrates. Prior to the growth, the substrates were cleaned with acetone and isopropanol, rinsed by deionized water and dried with nitrogen flow. Aluminum (Al) seed layer with different thicknesses (100 nm, 200 nm) were deposited on the substrates via thermal evaporation. The ZnO NWLs were grown in an aqueous solution of zinc nitrate hexahydrate (ZNH, $Zn(NO_3)_2 \cdot 6H_2O$) and hexamethylenetetramine (HMT, $(CH_2)_6N_4$) at 80° C. for 30 minutes. To study the effects of the chemical concentration on the morphology of the synthesized ZnO NWLs, several experiments were conducted using different molar ratios of ZNH and HMT (2:1, 1:1 and 1:2). For these experiments, a constant ZNH concentration of 25 mM was used with the total solution volume of 40 mL. After finishing the growth, the samples were removed from the solution, rinsed with DI water and dried with nitrogen. The effects of thermal annealing at elevated temperatures $T_{annealing}$=350° C., 600° C., 800° C.) for 3 hrs on the ZnO NWLs surface morphology and crystalline quality were also investigated.

Mechanical Transfer

Figure 15:
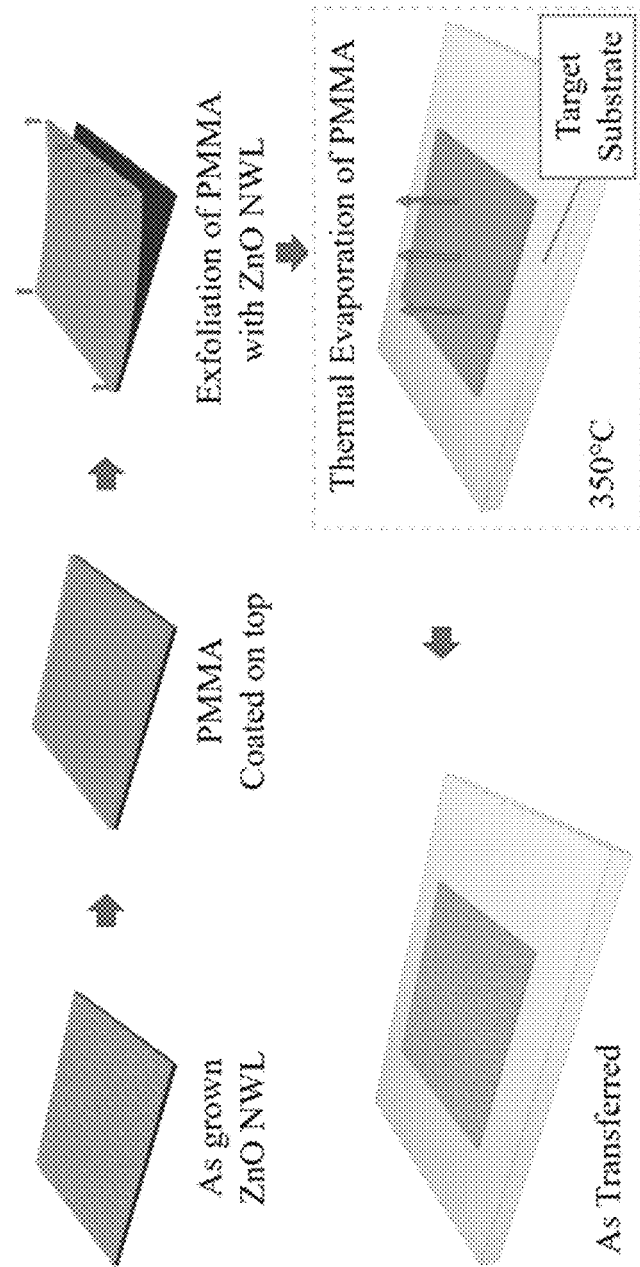
FIG. 15 is a schematic diagram of the mechanical transfer process for ZnO NWL.

The mechanical transfer process of the ZnO NWLs is illustrated in FIG. 15. PMMA solution (anisole as solvent, 7% concentration, MicroChem) was drop-coated on top of the grown sample and deposited uniformly by film applicator. Then the sample was dried on hot plate for 1 hr at 60° C. Using a blade, the PMMA film with ZnO NWLs attached was exfoliated from the growth substrate. The film was then embedded between two glass slides and put on hot plate for 2 hrs at 90° C. Heat curing of the film helped to release the strain and maintained the flatness of the PMMA film. After curing, the film was released from the glass slides and placed on the designated area of the target substrate. The film was hold in place on the substrate by anchoring its corners, protecting itself from disturbance in air. Furnace was then used to heat up and evaporate PMMA (350° C., 2 hrs) and left ZnO NWLs on the target substrate. The post-transferred ZnO NWLs were characterized by optical imaging and FESEM to demonstrate the integrity and effectiveness of the transfer process.

Piezoelectric Device Design and Fabrication

Figure 16:
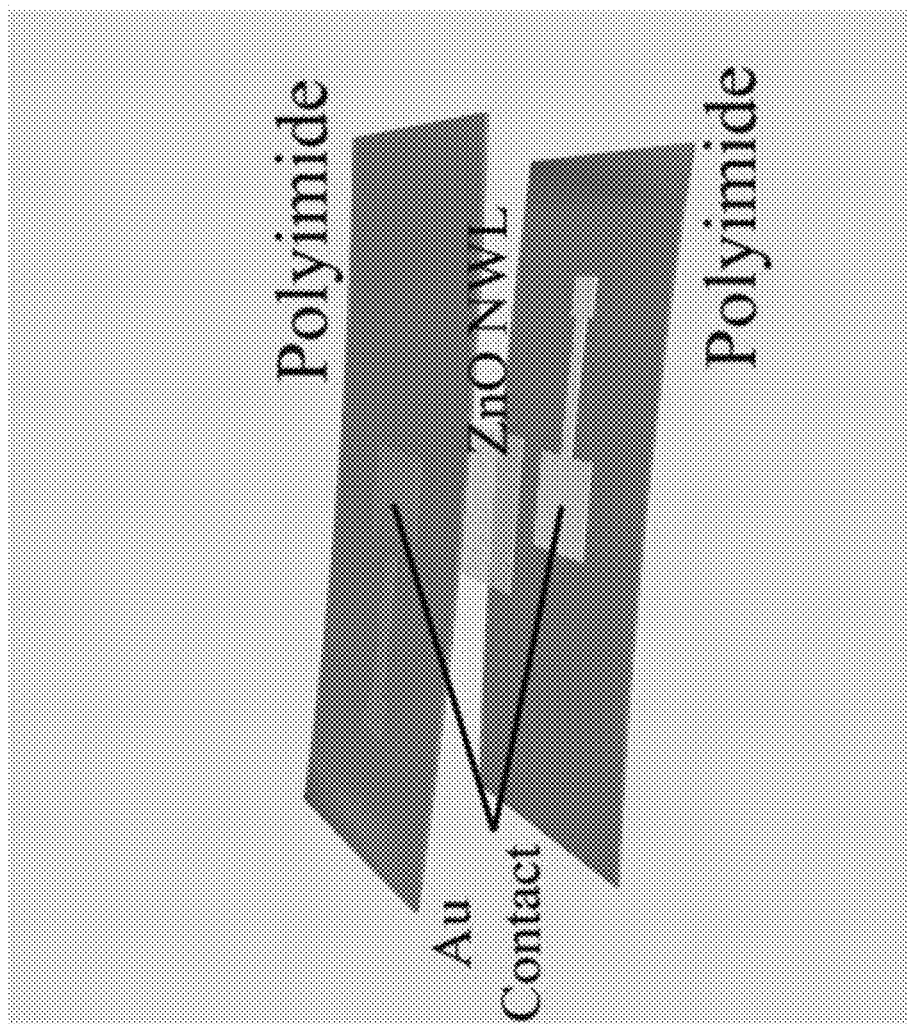
FIG. 16 is a schematic diagram of the prototype ZnO NWL piezoelectric device.

FIG. 16 shows the schematic of the prototype device. Polyimide (PI, HPP-ST 2 mil, Dupont) served as both top and bottom substrates and Ti/Au was deposited as contact. The size of the central contact area is 1 cm×1 cm. Au stripe of 3 mm wide is extended to one side of the substrate to serve as the contact pad for wirings. The ZnO NWL films were transferred to the bottom PI substrate and then packed with top substrate. The areas of the transferred films were larger (1.5 cm×1.5 cm) as compared to those of the Au contact pads, avoiding crosstalk between top and bottom contacts after transfer. Epoxy adhesive (Poxy Pak, Henkel) was applied on the edges of PI substrates for device packaging. Copper wires were connected to the outer contact pads to form extended connection. To confirm the sources of the voltage pulses, one reference device with no ZnO NWLs embedded in between the PI substrates was also fabricated. Numerical simulation was also conducted using COMSOL Multiphysics to study the piezoelectric properties of the ZnO NWLs.

Characterization

The morphology, crystalline quality and optical properties of the ZnO NWLs were characterized by using field emission scanning electron microscopy (FESEM), scanning electron microscopy (SEM), X-ray diffraction (XRD) and photoluminescence (PL) spectroscopy. FESEM images were taken with Helios 650. The SEM images were taken with Tescan Vega-3. XRD spectra were collected on a Bruker Discover D8 X-Ray Diffractometer with Cu Kα radiation (1.54 Å). PL spectra were measured at room temperature using a Jobin Yvon-spex-Fluorog-3-Spectrofluorimeter with a 450 W Xenon lamp as the light source. Piezoelectric voltage measurement was logged by Tektronic TPS 2024B Oscilloscope and retrieved through RS-232 port.

Results

Figure 17:
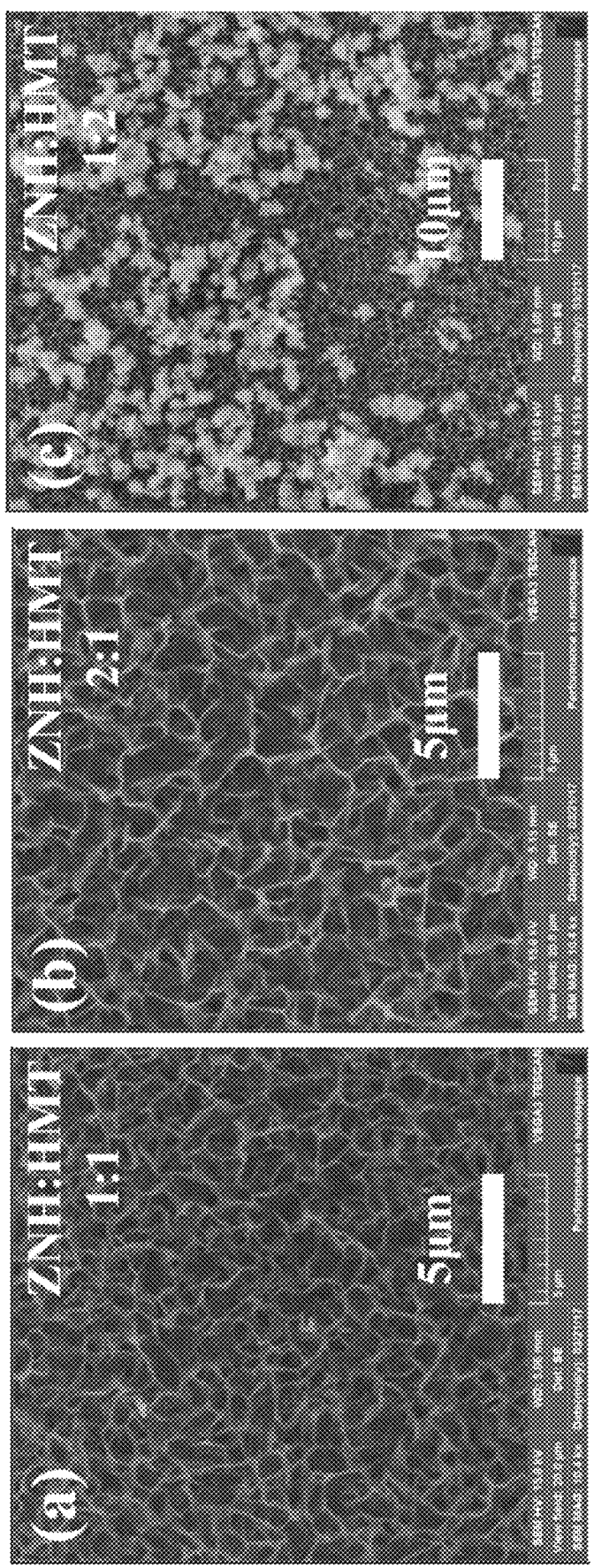
FIG. 17 illustrates top view scanning electron microscope (SEM) images of ZnO NWLs grown at 80 degrees Celsius on a $SiO_2$/Si substrate with three different ZNH:HMT molar ratios.

To study the effects of HMT molar concentration on the morphology of the synthesized ZnO NWLs, syntheses were conducted at 80° C. for 30 mins. For all the experiments, the ZNH concentration was fixed at 25 mM while varying the HMT concentration in the range between 12.5 mM and 50 mM. FIG. 17 shows the top view SEM images of the as-grown ZnO NWLs on $SiO_2$-on-Si substrate covered with 100 nm Al film using different HMT concentrations (FIG. 17, element (a), element (b), element (c)). For HMT concentrations of 25 mM and 12.5 mM (FIG. 17, element (a) and FIG. 17, element (b)), the morphologies of the ZnO NWLs are similar. As the concentration of the HMT increases to 50 mM, the synthesis process resulted in the formation of flower-like ZnO nanoparticles on top of the NWLs networks. The higher concentration of HMT provides more $Zn(OH)_4^{2-}$ ions (Eqs. (1)-(3)) in the solution which leads to the fast nucleation of ZnO crystallites in different crystal orientations such as [10-10] orientation, which promotes the formation of nanoflowers. From this study, the optimum chemical concentration of ZNH and HMT (1:1) was determined for later solution synthesis.

$$(CH_2)_6N_4 + H_2O \rightarrow HCHO + NH_3 \qquad (1)$$

$$NH_3 + H_2O \rightarrow NH_4^+ + OH^- \qquad (2)$$

$$Zn^{2+} + OH^- \rightarrow Zn(OH)_4^{2-} \rightarrow ZnO \qquad (3)$$

To investigate the effects of Al seed layer thickness on the growth rate, cross sectional SEM was conducted. It is known that the use of Al seed layer is critical to promote the formation of NWL structure instead of nanorod structure. Al oxidizes in the solution and forms $AlO_2^-$ (Eq. (4)). The binding of $AlO_2^-$ to the $Zn^{2+}$ terminated surface suppresses the growth of ZnO along the [0001] polar orientation and thus promotes its growth in the lateral orientation.

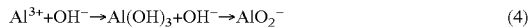
$$Al^{3+}+OH^-\rightarrow Al(OH)_3+OH^-\rightarrow AlO_2^- \quad (4)$$

FIG. 18 shows the cross-sectional SEM images of the ZnO NWLs grown on $SiO_2$-on-Si substrate with different Al thicknesses (100 nm FIG. 18, element (a) and 200 nm FIG. 18, element (b)) using the same concentration of ZNH and HMT (molar ratio=1:1). The growths were conducted for 30 mins. The ZnO NWLs grown on the 100 nm thick Al layer had a thickness of ~1.6 μm, which corresponds to a growth rate of ~3.2 μm/hr. On the other hand, the ZnO NWLs grown on 200 nm thick Al layer had a thickness of ~3.3 μm which corresponds to a growth rate of ~6.4 μm/hr. Previous studies indicate that the ZnO NWLs growth rate increases with the increase of the seed layer thickness, due to the increase of the $AlO_2^-$ concentration in the solution. However, for both cases, the formation of the nanoparticles on top of the NWLs occurs with longer growth time. This indicates the shift of growth kinetic from the formation of nanowalls to nanoflowers due to the decrease of $AlO_2^-$ concentration while the precipitation of ZnO is still fast. This is due to the screening of Al film by NWLs as it grows.

To study the effects of the growth substrate on the ZnO NWLs morphology, ZnO NWLs were synthesized on different substrates: $SiO_2$-on-Si ($SiO_2$/Si), Si (100), Si (111), PET and PI. The growth was conducted at 80° C. for 30 mins using 1:1 molar ratio of ZNH and HMT. The Al seed layer thickness was 100 nm. The surface morphologies of the as-synthesized ZnO NWLs on different substrates were similar. This indicates the flexibility of the substrate selection for the hydrothermal synthesis of ZnO NWLs for various applications.

Figure 19:
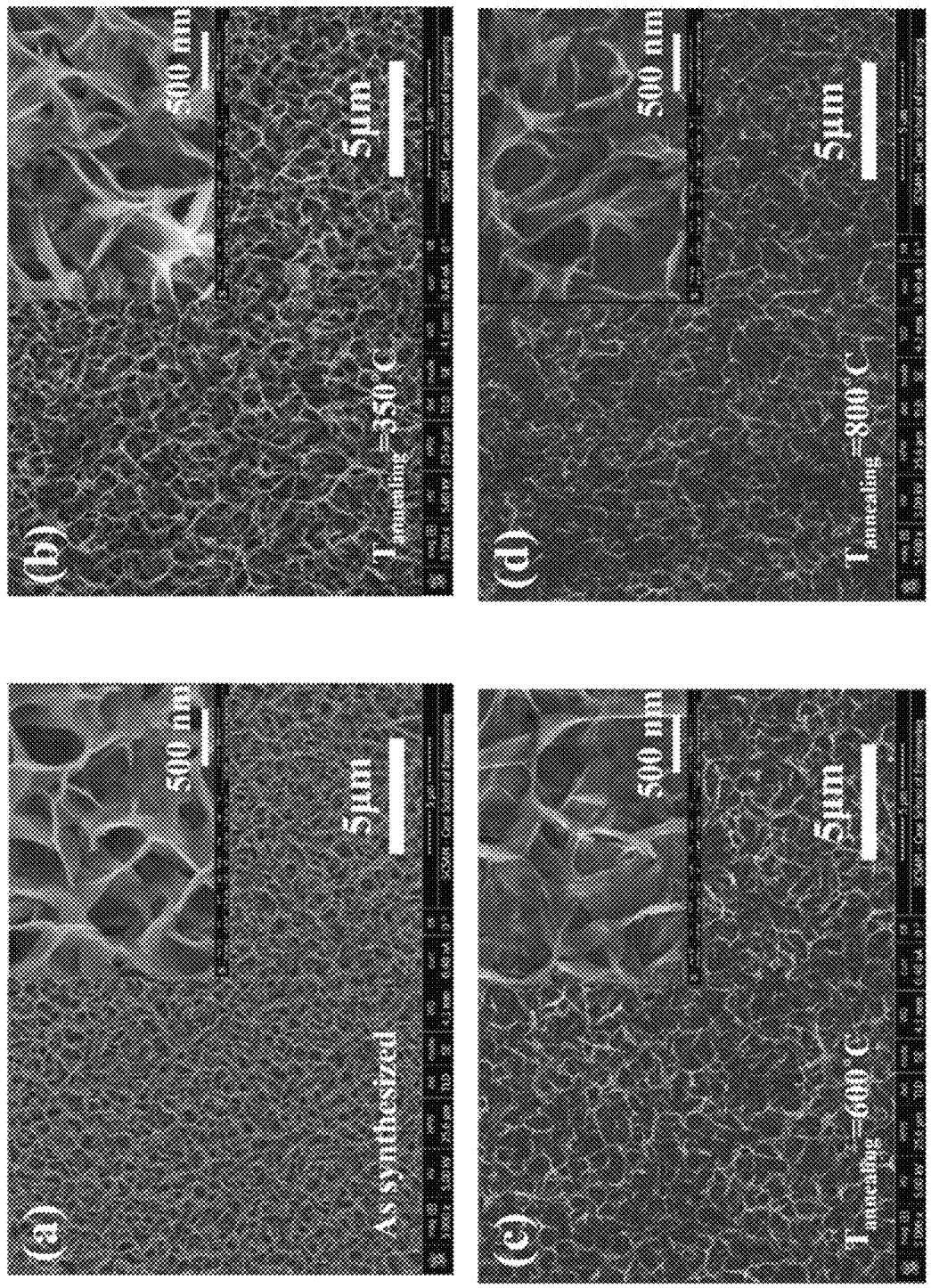
FIG. 19 illustrates top view field emission (FE) SEM images of ZnO NWLs annealed at different temperatures.

Due to the large defect concentration in hydrothermal synthesized ZnO materials, a thermal annealing process is typically utilized to improve the crystalline quality of the material, thus to improve the piezoelectric properties of the material for sensor device application. To study the effects of thermal annealing on the surface morphology, crystalline quality and optical properties of the synthesized ZnO NWLs, several annealing experiments were conducted at different temperatures (350° C., 600° C. and 800° C.). All the experiments were conducted under the flow of oxygen and argon for 3 hrs. FIG. 19 shows the top view SEM images of the as-grown and annealed ZnO NWLs with different annealing temperatures. As can be seen from the images, ZnO NWL structure regresses with increased annealing temperature. This indicates the ZnO NWLs tends to agglomerate during high temperature annealing process.

Figure 20:
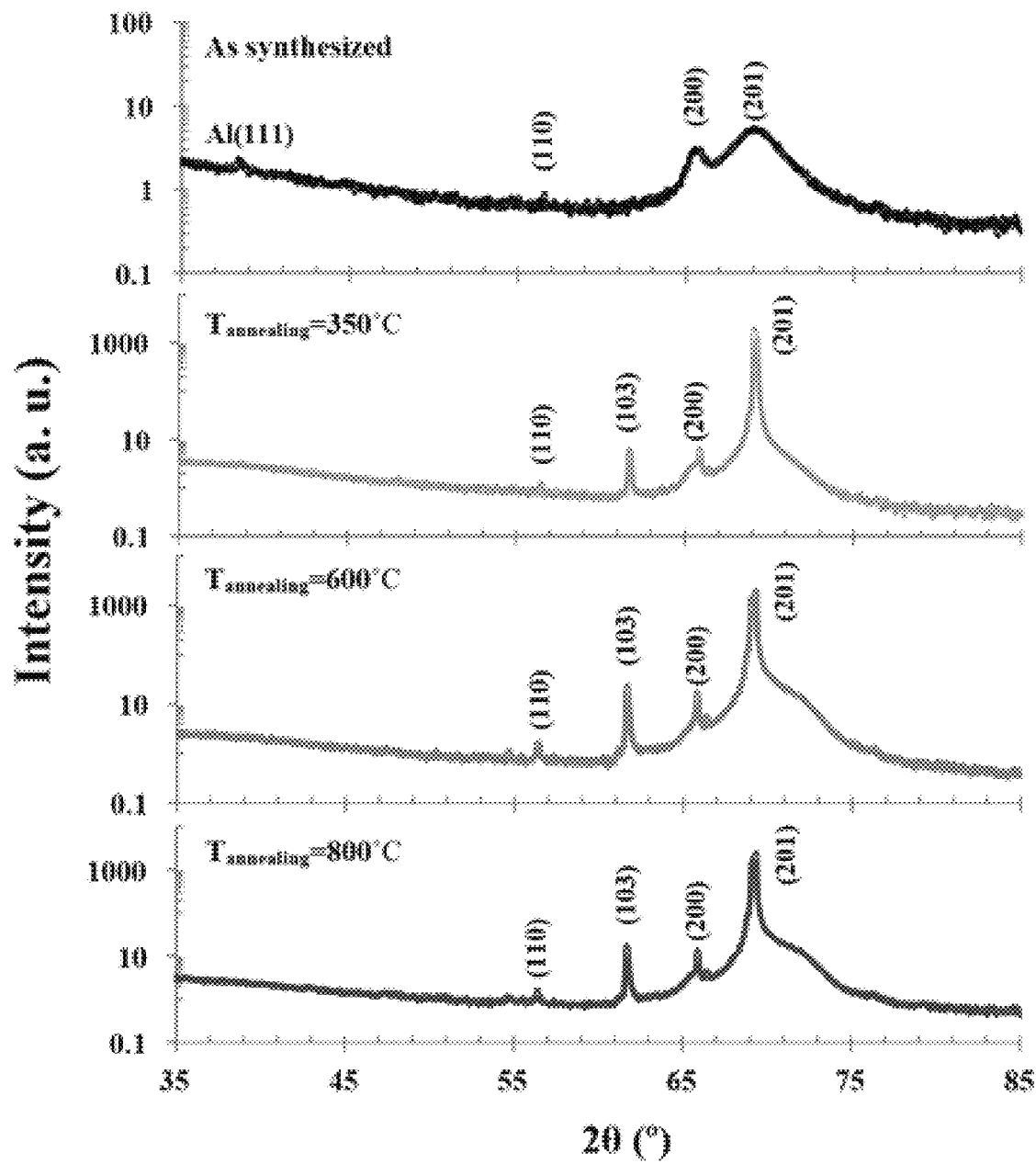
FIG. 20 shows X-ray powder diffraction (XRD) spectra ($\theta$-2$\theta$ scan) of ZnO NWLs.

FIG. 20 shows plots of the XRD spectra of the as-grown ZnO NWLs as compared to the materials after annealing at different temperatures. The as grown and annealed ZnO NWLs show polycrystalline properties with wurtzite ZnO structure. For all the spectra, ZnO (110), (200) and (201) peaks are clearly visible. After thermal annealing, ZnO (103) peak appeared, and the NWLs exhibited sharp (201) peak with higher intensity. The intensities of the (110), (103), and (200) peaks also increased with increasing annealing temperature. This indicates that high-temperature thermal annealing can improve the crystalline quality of the ZnO NWLs.

Figure 21:
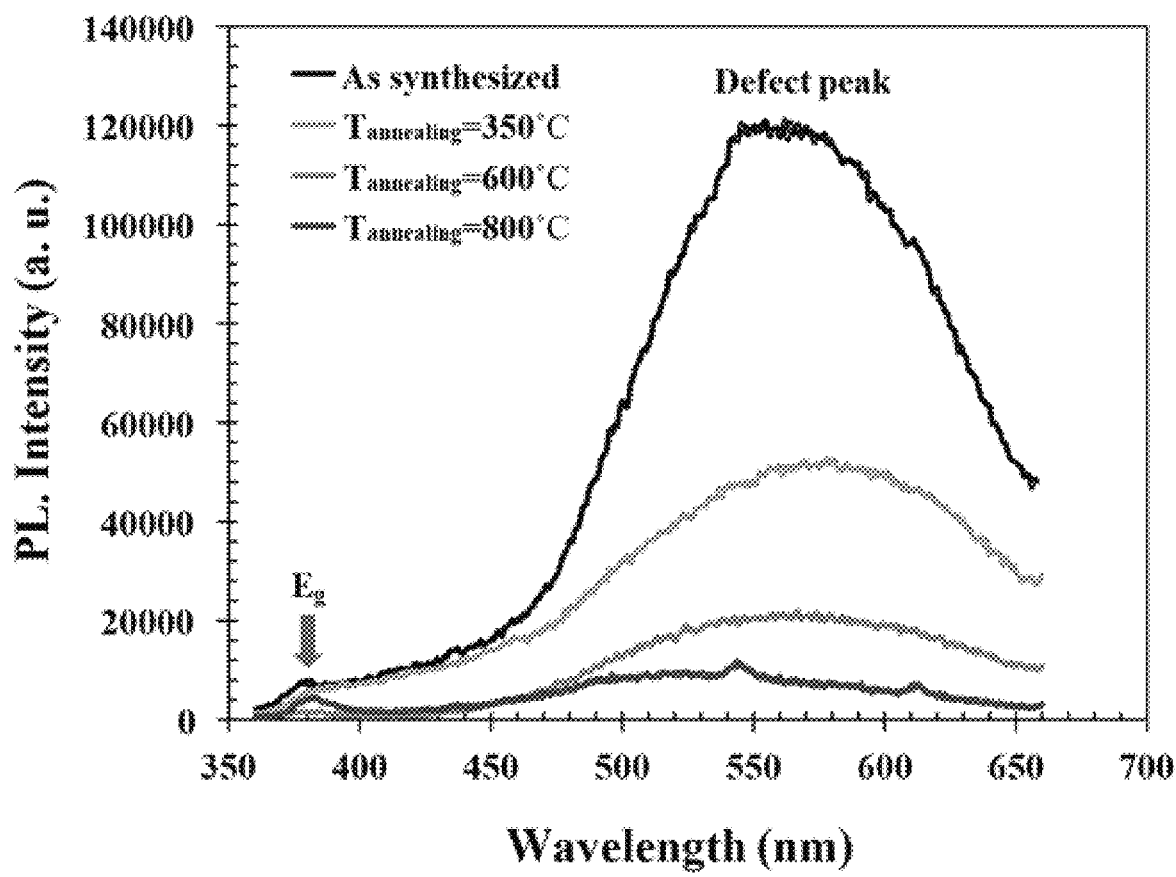
FIG. 21 shows room temperature photoluminescence (PL) spectra of ZnO NWLs.

FIG. 21 shows the PL spectra of the as-grown and annealed ZnO NWLs. The NWLs exhibited near band edge emission at ~380 nm and broad deep level emission around 540-580 nm. As the annealing temperature increases, the overall intensity of the spectrum decreases, which is partially due to the reduced NWL thickness as NWLs agglomerate. Note that the intensity of the green luminescence reduces significantly as the annealing temperature increases. It has been reported previously that the green emission is related to the oxygen vacancies ($V_O$) in ZnO. The relatively high intensity of the green emission peak in the as-grown ZnO NWLs is due to the strong bonding between Al and O leading to high density of $V_O$. With the thermal annealing under oxygen atmosphere, the reduction of $V_O$ contributed to the reduction of the intensity of green emission peak.

From systematic studies, the optimal synthesis condition of ZnO NWLs (ZNH:HMT=1:1) and growth substrate ($SiO_2$/Si with 200 nm Al seed layer) for the studies of mechanical transfer process were identified. Since thermal annealing process enhances the crystalline quality of the material, different annealing temperatures (350° C., 600° C., 800° C. for 3 hr) for ZnO NWLs were tried prior to the transfer process. It was observed that high annealing temperature tends to build strong bonding between ZnO NWLs and its growth substrate, making the exfoliation process challenging. Mechanical transfer of ZnO NWL with Tannealing>600° C. causes significant damage to the film and consequently deteriorates the performance of the device. Thus, Tannealing=600° C. was identified as the optimum temperature of thermal annealing for transfer process. FIG. 22, element (a) shows the photo image of the ZnO NWLs transferred to the Si substrate. The size of the transferred NWL film was 1.5 cm×1.5 cm. Note that there were cracks on the transferred NWL film. These defects were caused by the scratching from the blade during the exfoliation process. As shown in the SEM image of FIG. 22, element (b), the surface morphology of the ZnO NWLs was maintained after the transfer process.

Figure 24:
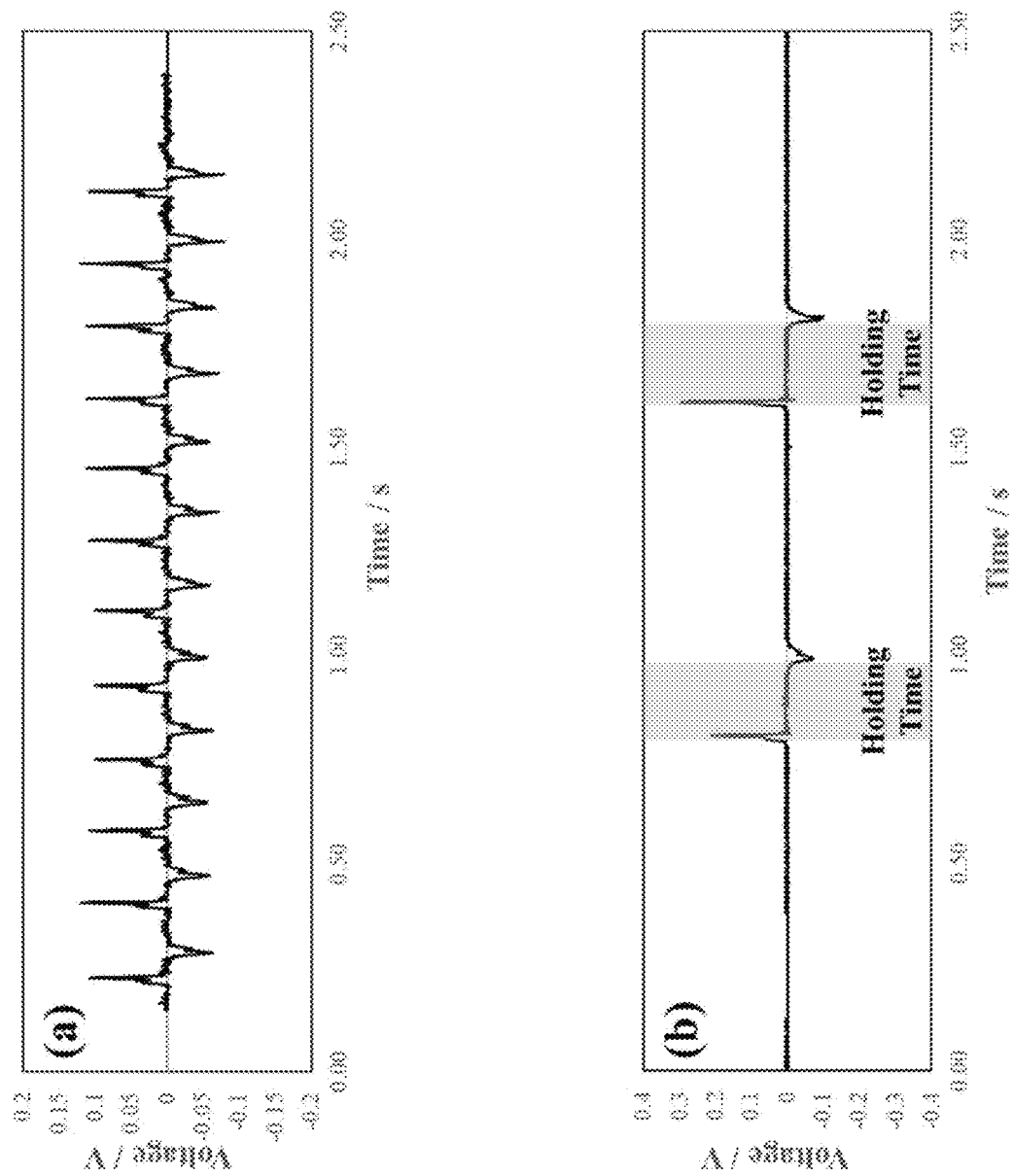
FIG. 24 shows recorded representative voltage-over-time log for a ZnO NWLs device with periodically applied pressure on the device and delayed release of pressure on the device.

To demonstrate the piezoelectricity of the transferred ZnO NWLs, the prototype devices were fabricated. FIG. 23 shows the prototype device fabricated on flexible PI substrate. The voltage output characteristic for a typical device is shown in FIG. 24, element (a). As shown in the figure, pulse signals were generated with periodically applied finger force on top of the device. FIG. 24, element (b) plots the output signal as a function of time and with applied external force and delayed release. The positive output signal with applied force is from the compressive deformation of the ZnO NWLs, and the negative signal with the release of the external force is caused by material restoration. The maximum output voltage recorded was ~300 mV from the finger applied force. These devices showed similar output voltage characteristics as compared to the previously reported nanogenerators fabricated using ZnO nanorods and ZnO nanowalls. For the reference device with no NWLs embedded between the electrodes, no output voltage was observed.

To study the piezoelectric properties of the ZnO NWLs, COMSOL Multiphysics was used to develop a model with a honeycomb-like structure. The simulated device is composed of ZnO hollow hexagon structure with electrodes at the top and bottom. Periodic boundary conditions were set on the sidewalls of the single hexagonal unit, sharing the boundary condition of deformation, elastic strain and electric potential with 6 neighboring hexagon units (see Supporting Information). Three geometric parameters were specified: nanowall height (h), nanowall lateral length (a), and nanowall thickness (t). In the simulation, the vertical pressure was applied on top of the device. The bottom electrode was fixed in position and electrically grounded. The potential difference between the top and bottom electrodes was calculated.

Based on the synthesized ZnO NWL structure, the following parameters were used in the simulation: a=250 nm, t=50 nm, h=2.5 µm. These parameters were extracted from experimental characterization of the grown ZnO NWLs. From the simulation results, the voltage output was observed to be linearly proportional to both applied pressure and nanowall height. This is due to the deformation of ZnO NWLs in the vertical direction under applied force. A larger deformation builds up higher piezoelectric potential between the top and bottom electrodes. The electric potential of the hexagonal unit cell was modeled with the periodic boundary condition. With an approximate 10 N of applied force and 0.5 cm×0.5 cm contact area during the device test, 400 kPa was estimated as the typical pressure applied to the devices under test. In the simulation, with the set pressure of 400 kPa, the corresponding output voltage is ~210 mV. The simulation results are consistent with the experimental data.

From the above description, those skilled in the art will perceive improvements, changes and modifications. Such improvements, changes and modifications are within the skill of one in the art and are intended to be covered by the appended claims.

The following is claimed:

1. A system comprising:
   a socket for a prosthetic device, wherein the socket is configured to fit a patient's residual limb; and
   an inner socket sensor array configured to be positioned within the socket for the prosthetic device and to detect pressure of the socket on the patient's residual limb and/or shear force of the socket on the patient's residual limb, the inner socket sensor array comprising:
   a first plurality of uniformly distributed metal pads distributed on a first flexible substrate,
   a second plurality of uniformly distributed metal pads distributed on a second flexible substrate, the second plurality of uniformly distributed metal pads having an equal number to the first plurality of uniformly distributed metal pads and configured so a metal pad of the first plurality of uniformly distributed metal pads opposes a metal pad of the second plurality of uniformly distributed metal pads,
   a thin sheet of piezo-electric material comprising a zinc oxide nanowall structure having a hollow hexagonal morphological structure, configured to be sandwiched between the first plurality of uniformly distributed metal pads and the second plurality of uniformly distributed metal pads, wherein data related to the pressure and/or the shear force is based on a resistance of at least a portion of the thin sheet of piezo-electric material; and
   a common port connected to each of the metal pads of the first and second pluralities of uniformly distributed metal pads by at least one wire.

2. The system of claim 1, further comprising a signal processing circuit to receive the data related to the pressure and/or shear force from the inner socket sensor array through the common port and processes the data related to the pressure and/or shear force to facilitate creation of a pressure map based on the data related to the pressure and/or shear force for visualization on a mobile computing device.

3. The system of claim 2, wherein the signal processing circuit is connected to at least one of the inner socket sensor array and the mobile computing device by a wireless connection.

4. The system of claim 3, wherein the wireless connection is a short-range wireless connection.

5. The system of claim 2, wherein the signal processing circuit comprises at least one multiplexer, a voltage divider circuit, an analog-to-digital convertor, a control unit, a power management unit, and a data transmission unit.

6. The system of claim 1, wherein the pressure and/or shear force are detected continuously.

7. The system of claim 1, wherein the inner socket sensor array is customizable to different sizes depending on a socket size.

8. The system of claim 1, wherein at least one of the metal pads in the first and second pluralities of uniformly distributed metal pads comprises copper.

9. The system of claim 1, further comprising a liner configured to be worn over the patient's residual limb to separate the patient's residual limb and the socket.

10. The system of claim 9, wherein the liner comprises at least one of an electrically active polymer (EAP) and a moisture-wicking material.

* * * * *